United States Patent
Amis et al.

(10) Patent No.: US 11,436,731 B2
(45) Date of Patent: Sep. 6, 2022

(54) LONGITUDINAL DISPLAY OF CORONARY ARTERY CALCIUM BURDEN

(71) Applicant: LightLab Imaging, Inc., Westford, MA (US)

(72) Inventors: Gregory Patrick Amis, Westford, MA (US); Ajay Gopinath, Bedford, MA (US); Mark Hoeveler, Eliot, ME (US)

(73) Assignee: LightLab Imaging, Inc., Westford, MA (US)

( * ) Notice: Subject to any disclaimer, the term of this patent is extended or adjusted under 35 U.S.C. 154(b) by 126 days.

(21) Appl. No.: 16/985,623

(22) Filed: Aug. 5, 2020

(65) Prior Publication Data
US 2021/0042927 A1   Feb. 11, 2021

Related U.S. Application Data

(60) Provisional application No. 62/883,066, filed on Aug. 5, 2019.

(51) Int. Cl.
*G06T 7/00* (2017.01)
*G06T 7/38* (2017.01)
(Continued)

(52) U.S. Cl.
CPC ........ *G06T 7/0016* (2013.01); *A61B 5/02007* (2013.01); *A61B 5/7264* (2013.01);
(Continued)

(58) Field of Classification Search
CPC ........ G16H 30/40; G16H 50/30; G16H 50/50; G06T 11/008; G06T 2207/10068;
(Continued)

(56) References Cited

U.S. PATENT DOCUMENTS

| 7,907,766 B2 | 3/2011 | Lehel et al. |
| 8,970,578 B2 | 3/2015 | Voros et al. |

(Continued)

FOREIGN PATENT DOCUMENTS

| CN | 103462696 A | 12/2013 |
| CN | 107945176 A | 4/2018 |

(Continued)

OTHER PUBLICATIONS

Guagliumi et al., Volumetric assessment of lesion severity with optical coherence tomography: relationship with fractional flow reserve, Euro Intervention, Feb. 2013, vol. 8, pp. 1172-1181 (12 pages total).

(Continued)

*Primary Examiner* — Manuchehr Rahmjoo
(74) *Attorney, Agent, or Firm* — Lerner, David, Littenberg, Krumholz & Mentlik, LLP

(57) ABSTRACT

The present disclosure provides systems and methods to receiving OCT or IVUS image data frames to output one or more representations of a blood vessel segment. The image data frames may be stretched and/or aligned using various windows or bins or alignment features. Arterial features, such as the calcium burden, may be detected in each of the image data frames. The arterial features may be scored. The score may be a stent under-expansion risk. The representation may include an indication of the arterial features and their respective score. The indication may be a color coded indication.

15 Claims, 14 Drawing Sheets

(51) Int. Cl.
  *G16H 50/50* (2018.01)
  *G16H 50/30* (2018.01)
  *G16H 30/40* (2018.01)
  *A61B 5/02* (2006.01)
  *A61B 5/00* (2006.01)
  *G06T 11/00* (2006.01)

(52) U.S. Cl.
  CPC ............ *A61B 5/7275* (2013.01); *A61B 5/743* (2013.01); *G06T 7/38* (2017.01); *G06T 11/008* (2013.01); *G16H 30/40* (2018.01); *G16H 50/30* (2018.01); *G16H 50/50* (2018.01); *G06T 2207/20081* (2013.01); *G06T 2207/30104* (2013.01)

(58) Field of Classification Search
  CPC . G06T 2207/20081; G06T 2207/30101; G06T 2207/30104; G06T 7/0012; G06T 7/0016; G06T 7/38; A61B 5/02007; A61B 5/7264; A61B 5/7275; A61B 5/743
  See application file for complete search history.

(56) References Cited

U.S. PATENT DOCUMENTS

| | | | |
|---|---|---|---|
| 9,043,190 | B2 | 5/2015 | Grady et al. |
| 9,173,591 | B2 | 11/2015 | Elbasiony et al. |
| 9,679,374 | B2 | 6/2017 | Choi et al. |
| 2005/0043614 | A1 | 2/2005 | Huizenga et al. |
| 2008/0159610 | A1 | 7/2008 | Haas et al. |
| 2009/0129661 | A1 | 5/2009 | Licato |
| 2014/0114618 | A1 | 4/2014 | Fonte et al. |
| 2016/0157787 | A1 | 6/2016 | Merritt et al. |
| 2016/0157805 | A1 | 6/2016 | Bathina et al. |
| 2017/0071671 | A1 | 3/2017 | Neumann et al. |
| 2018/0271614 | A1* | 9/2018 | Kunio ............... A61B 90/37 |
| 2018/0315182 | A1 | 11/2018 | Rapaka et al. |
| 2019/0172197 | A1 | 6/2019 | Buckler et al. |
| 2019/0180438 | A1 | 6/2019 | Buckler et al. |
| 2019/0282182 | A1 | 9/2019 | Scott et al. |
| 2019/0282211 | A1 | 9/2019 | Merritt et al. |
| 2019/0318476 | A1 | 10/2019 | Isgum et al. |
| 2020/0029861 | A1 | 1/2020 | Rajguru et al. |
| 2020/0029932 | A1 | 1/2020 | Cohen et al. |
| 2020/0142575 | A1 | 5/2020 | Gopinath et al. |

FOREIGN PATENT DOCUMENTS

| | | |
|---|---|---|
| CN | 109035215 A | 12/2018 |
| CN | 109036551 A | 12/2018 |
| CN | 110222759 A | 9/2019 |
| CN | 111265252 A | 6/2020 |
| CN | 111768403 A | 10/2020 |
| DE | 102008003940 A1 | 7/2008 |
| EP | 3132749 A1 | 2/2017 |
| WO | 2007109771 A2 | 9/2007 |
| WO | 2009032206 A1 | 3/2009 |
| WO | 2014022804 A1 | 2/2014 |
| WO | 2017216645 A2 | 12/2017 |
| WO | 2019197450 A1 | 10/2019 |
| WO | 2020222004 A1 | 11/2020 |
| WO | 2020234232 A1 | 11/2020 |
| WO | 2020234233 A1 | 11/2020 |

OTHER PUBLICATIONS

Nakamura et al., New Volumetric Analysis Method for Stent Expansion and its Correlation With Final Fractional Flow Reserve and Clinical Outcome, JACC:Cardiovascular Interventions, Aug. 2018, pp. 1467-1478, vol. 11, No. 15.

Ali, Z., et al., "Optical Coherence Tomography Compared with Intravascular Ultrasound and with Angiography to Guide Coronary Stent Implantation (Ilumien III: Optimize PCI): A Randomised Controlled Trial," Lancet, Oct. 30, 2016, pp. 2619-2628, vol. 388.

Fujino, A., et al., "A New Optical Coherence Tomography-based Calcium Scoring System to Predict Stent Underexpansion," EuroIntervention, Apr. 6, 2018, pp. e2182-e2189, vol. 13, No. 18.

Shlofmitz, et al., "Calcified Plaque," NCBI Bookshelf. A service of the National Library of Medicine, National Institutes of Health, Apr. 24, 2020, pp. 1-5, StatPearls Publishing LLC.

Alberti M, Balocco S, Carrillo X, Mauri J, Radeva P. "Automatic non-rigid temporal alignment of IVUS sequences." Ayache N. Delingette H. Golland p. Mori K. (Eds), InInternational Conference on Medical Image Computing and Computer-Assisted Intervention, vol. 7510, Oct. 1, 2012 (pp. 642-650). ISBN: 978-3-642-17318-9, Springer, Berlin, Heidelberg.

International Search Report including Written Opinion for PCT/US2020/044995 dated Nov. 11, 2020; 18 pages.

* cited by examiner

LONGITUDINAL DISPLAY OF CORONARY ARTERY CALCIUM BURDEN

CROSS-REFERENCE TO RELATED APPLICATIONS

The present application claims the benefit of the filing date of U.S. Provisional Patent Application No. 62/883,066 filed Aug. 5, 2019, the disclosure of which is hereby incorporated herein by reference.

BACKGROUND

Generally, coronary artery plaques are fibrotic, lipidic, calcified, thrombotic, or some combination thereof. Calcified plaques pose a particular risk to successful treatment, as they do not always permit full expansion of a balloon during stenting or angioplasty, and thus it is critical that physicians identify calcium and treat it appropriately. Typically optical coherence tomography (OCT) is especially helpful in identifying plaque composition at each cross-sectional frame. OCT and other imaging modalities can be used to assess various arterial features.

Calcification of a coronary artery plaque can prevent a stent from fully expanding. An under-expanded stent increases the risk of in-stent restenosis and the need for future treatment. It is therefore critical that interventional cardiologists recognize this risk and adapt their treatment strategy accordingly. However, current standard practice and state of the art does not provide physicians with adequate tools to quantify the risk. Angiography, near-infrared spectroscopy, and OCT help visualize calcium deposits, and there exists manual rules-of-thumb to estimate under expansion risk, but the risk remains under-quantified and under-appreciated.

BRIEF SUMMARY

One aspect of the present disclosure is a method of displaying one or more arterial features relative to a first pullback representation and a second pullback representation comprising receiving, by one or more processors, a first group of frames and a second group of frames, detecting, by the one or more processors, an arterial feature in each frame of the first group of frames and the second group of frames, scoring, by the one or more processors, the detected arterial feature in each frame of the first group of frames and the second group of frames and outputting, by the one or more processors, a representation of the first group of frames and the second group of frames, wherein the output includes a visual indication of a difference between the score of detected arterial feature in at least one frame of the first group of frames and at least one frame of the second group of frames or a change in the detected arterial features in the at least one frame of the first group of frames and the at least one frame of the second group of frames.

The first group of frames may be obtained from a first pullback and the second group of frames is obtained from a second pullback different than the first pullback.

The method may further comprise aligning by the one or more processors, the at least one frame of the first group of frames with the at least one frame of the second group of frames based on the score of the detected arterial feature in the at least one frame of the first group of frames and the score of the detected arterial feature of the at least one frame of the second group of frames.

Outputting a representation may further include outputting, by the one or more processors, at least one value, indicia, or visual cue, and the at least one value, indicia, or visual clue may include color or hashing. The color may be a color code base on the score of the detected arterial feature. The detected arterial feature may be a calcium burden. Scoring the calcium burden may be based on a determined calcium arc or a determined calcium volume.

The method may further comprise predicting, by the one or more processors based on a scored calcium burden, stent expansion on a per frame basis.

Another aspect of the disclose includes a method comprising receiving, by one or more processors, one or more frames including image data of a blood vessel segment, detecting, by the one or more processors, an arterial feature in each of the one or more frames, scoring, by the one or more processors, the arterial feature in each of the one or more frames, identifying, by the one or more processors based on the arterial feature score, a region of interest, and outputting, by the one or more processors based on the arterial feature score, a representation of the blood vessel segment including a visual indication of the score for the region of interest.

The detected arterial feature may be a calcium burden. The arterial feature score may be an under-expansion score. The under-expansion risk may be determined, by the one or more processors, using a machine learning model. The machine learning model may compare pre-percutaneous coronary intervention ("PCP") data and post-PCI data for a plurality of cases.

The under-expansion risk may be a stent under-expansion risk. The visual indication of the stent under-expansion risk may be a color-coded indication. The color-coded indication may be based on a severity of the under-expansion risk.

Scoring the arterial feature in each of the one or more frames may be based on a sliding window measure. The visual indication of the score may be a bar parallel to a longitudinal axis of the representation of the blood vessel and extends along the region of interest. The bar may be color-coded based on the arterial feature score. The arterial feature score may be a stent under-expansion risk.

DETAILED DESCRIPTION

Figure 1A:
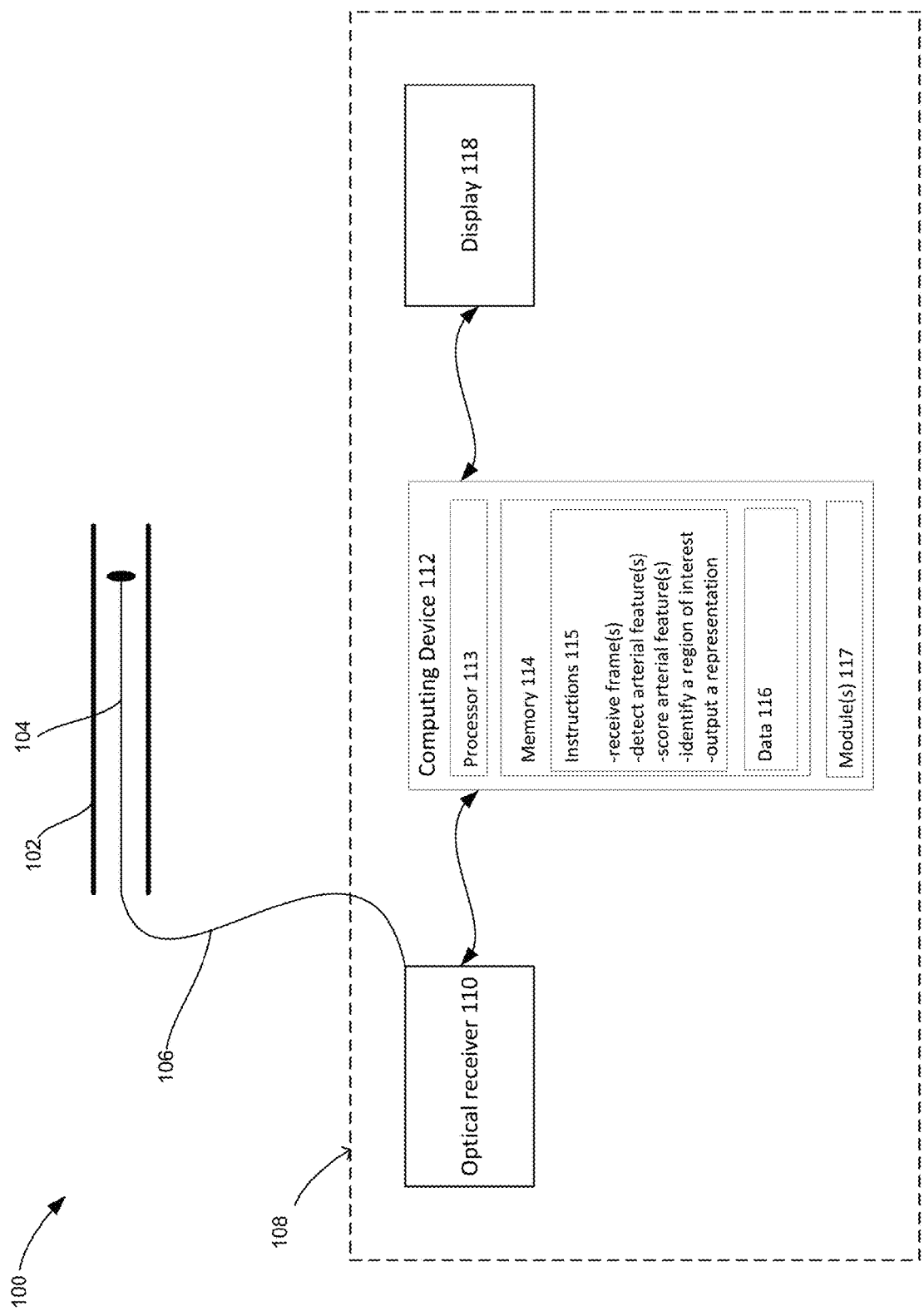
FIG. 1A is an example system according to aspects of the disclosure.

Some portions of the detailed description are presented in terms of methods such as algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value. All numerical values and ranges disclosed herein are deemed to include "about" before each value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Introduction

Systems and methods may perform feature detection and alignment of relative imaging datasets from an intravascular imaging pullback. For example, the intravascular imaging pullback may be an OCT or intravascular ultrasound ("IVUS") pullback. The imaging data sets may be taken at one or more points in time corresponding to different arterial events or treatments. One or more representations of an artery may be displayed based on the imaging data set. The representations may include an indication of identification of calcium burden after performing calcium detection on one or more (a group or subset) of image data frames. The one or more representations may be displayed to a user.

Image processing techniques and/or machine learning may detect calcium in the image data. The frames of the pullback may be stretched and aligned using various windows or bins of alignment features. The alignment may be informed or optimized using various inputs or constrains such as: flexibility to stretch pullback using lumen data frames or other data in order to maximize alignment, points for lining up calcium edges, points for lining up stents, and points for lining up side branches (SBs).

The detection of calcium, or other features or tissue qualities, of interest may be performed. The detected features may then be identified as a cluster or group. The clusters or groups of the detected features may be displayed relative to one or more pullbacks over time. For example, the pullbacks may be taken pre-treatment, post-treatment, pre-stenting, post-stenting, pre-artherectormy, post-artherectomy, pre-angioplasty, post-angioplasty, post-optimization, etc. According to some examples, the pullbacks may be taken after stenting and/or after the physician has further ballooned the stent with various balloon diameters and pressures. The pullbacks may be aligned using common features identified in each of the frames. The common features may include, for example, side branches, stents, prior stents and other features using the techniques disclosed herein.

Information pertaining to the lumen profile, detected stents, measurements of the minimum lumen area, mean lumen area, minimal stent area ("MSA"), etc. may be displayed. The display may also include a risk level pertaining to the calcium burden. In some examples, the risk level may be the risk of stent under-expansion posed by the calcium burden. The risk of stent under-expansion may be automatically estimated and/or calculated based on the determined calcium burden.

The display may include a longitudinal view of the blood vessel. According to some examples, the display may highlight regions of calcium burden in the blood vessel. The calcium burden begins as a lesion. The lesion may begin as lipid and may gradually harden into a combination of fibrous and calcified plaque. As the lesion calcifies, the lesion may harden and may become more resistant to stent expansion. Different calcium scoring techniques may be used to improve decision making such as where to land stents or where to perform angioplasty or artherectomy.

The display may also include views of calcium burden within an OCT pullback of a blood vessel, such as a coronary artery. A variety of different outputs that may be displayed. For example, there may be one or more horizontal charts. The horizontal charts may include a key for identifying the color of the display. However, in some examples, the display may not include a key as the display may be a color display and, therefore, a key may not be needed.

The charts may plot calcium burden with the OCT pullback frame number on the x axis and the calcium burden level on the y axis. The charts may illustrate that there are eight different calcified plaques shown during the pullback. According to one, only one of the calcified plaques may be high red "R." A calcified plaque identified as red "R" may indicate that the calcified plaque should be looked at when determining a pre- and/or post-treatment plan. According to some examples, calcified plaque identified as red "R" may be calcified plaque that is likely to pose a problem for stent expansion. Other labelled calcified plaques, such as those labeled orange "O," may indicate that the calcified plaque may be worth looking at when determining a pre- and/or post-treatment plan. Calcified plaque labeled green "G," may be calcified plaques that are not likely going to pose a problem to stent expansion and, therefore, may not be worth looking at when determining a pre- and/or post-treatment plan.

Example Systems

FIG. 1A illustrates a data collection system 100 for use in collecting intravascular data. The system may include a data collection probe 104 that can be used to image a blood vessel 102. A guidewire, not shown, may be used to introduce the probe 104 into the blood vessel 102. The probe 104 may be introduced and pulled back along a length of a blood vessel while collecting data. As the probe 104 is pulled back, or retracted, a plurality of scans or OCT and/or IVUS data sets may be collected. The data sets, or frames of image data, may be used to identify features, such as calcium.

The probe 102 may be connected to a subsystem 108 via an optical fiber 106. The subsystem 108 may include a light source, such as a laser, an interferometer having a sample arm and a reference arm, various optical paths, a clock generator, photodiodes, and other OCT and/or IVUS components.

The probe 102 may be connected to an optical receiver 110. According to some examples, the optical receiver 110 may be a balanced photodiode based system. The optical receiver 31 may be configured to receive light collected by the probe 102.

The subsystem may include a computing device 112. The computing device may include one or more processors 113, memory 114, instructions 115, data 116, and one or more modules 117.

The one or more processors 113 may be any conventional processors, such as commercially available microprocessors. Alternatively, the one or more processors may be a dedicated device such as an application specific integrated circuit (ASIC) or other hardware-based processor. Although FIG. 1B functionally illustrates the processor, memory, and other elements of device 110 as being within the same block, it will be understood by those of ordinary skill in the art that the processor, computing device, or memory may actually include multiple processors, computing devices, or memories that may or may not be stored within the same physical housing. Similarly, the memory may be a hard drive or other storage media located in a housing different from that of device 112. Accordingly, references to a processor or computing device will be understood to include references to a collection of processors or computing devices or memories that may or may not operate in parallel.

Memory 114 may store information that is accessible by the processors, including instructions 115 that may be executed by the processors 113, and data 116. The memory 114 may be a type of memory operative to store information accessible by the processors 113, including a non-transitory computer-readable medium, or other medium that stores data that may be read with the aid of an electronic device, such as a hard-drive, memory card, read-only memory ("ROM"), random access memory ("RAM"), optical disks, as well as other write-capable and read-only memories. The subject matter disclosed herein may include different combinations of the foregoing, whereby different portions of the instructions 101 and data 119 are stored on different types of media.

Memory 114 may be retrieved, stored or modified by processors 113 in accordance with the instructions 115. For instance, although the present disclosure is not limited by a particular data structure, the data 115 may be stored in computer registers, in a relational database as a table having a plurality of different fields and records, XML documents, or flat files. The data 115 may also be formatted in a computer-readable format such as, but not limited to, binary values, ASCII or Unicode. By further way of example only, the data 115 may be stored as bitmaps comprised of pixels that are stored in compressed or uncompressed, or various image formats (e.g., JPEG), vector-based formats (e.g., SVG) or computer instructions for drawing graphics. Moreover, the data 115 may comprise information sufficient to identify the relevant information, such as numbers, descriptive text, proprietary codes, pointers, references to data stored in other memories (including other network locations) or information that is used by a function to calculate the relevant data.

The instructions 115 can be any set of instructions to be executed directly, such as machine code, or indirectly, such as scripts, by the processor 113. In that regard, the terms "instructions," "application," "steps," and "programs" can be used interchangeably herein. The instructions can be stored in object code format for direct processing by the processor, or in any other computing device language including scripts or collections of independent source code modules that are interpreted on demand or compiled in advance. Functions, methods and routines of the instructions are explained in more detail below.

The modules 117 may include a plaque, such as calcium plaque, detection module, a display module, stent detection or other detection and display modules. For example, the computing device 112 may access a calcification detection module for detecting the existence of a calcium plaque in the blood vessel. According to some examples, the modules may include an image data processing pipeline or component modules thereof. The image processing pipeline may be used to transform collected OCT data into two-dimensional ("2D") and/or three-dimensional ("3D") views and/or representations of blood vessels, stents, and/or detected regions.

The computing device 112 may include a machine learning module. Image data from previous cases may be collected and stored in data 116. Each of the frames of the previous cases may be analyzed to determine calcium burden and the effect on stent under-expansion. The analyzed information may be stored and used as input into a machine learning model. The machine learning model may predict a stent under-expansion risk. The machine learning model is further described below with respect to FIG. 5.

The subsystem 108 may include a display 118 for outputting content to a user. As shown, the display 118 is separate from computing device 112 however, according to some examples, display 118 may be part computing device 112. The display 118 may output image data relating to one or more features detected in the blood vessel. For example, the output may include, without limitation, cross-sectional scan data, longitudinal scans, diameter graphs, image masks, lumen border, plaque sizes, plaque circumference, visual indicia of plaque location, visual indicia of risk posed to stent expansion, etc. The display 118 may identify features with text, arrows, color coding, highlighting, contour lines, or other suitable human or machine readable indicia.

According to some examples the display 118 may be a graphic user interface ("GUI"). One or more steps may be performed automatically or without user input to navigate images, input information, select and/or interact with an input, etc. The display 118 alone or in combination with computing device 112 may allow for toggling between one or more viewing modes in response to user inputs. For example, a user may be able to toggle between different side branches on the display 118, such as by selecting a particular side branch and/or by selecting a view associated with the particular side branch.

In some examples, the display 118, alone or in combination with computing device 112, may include a menu. The menu may allow a user to show or hide various features. There may be more than one menu. For example, there may be a menu for selecting blood vessel features to display. Additionally or alternatively, there may be a menu for selecting the virtual camera angle of the display.

Figure 1B:
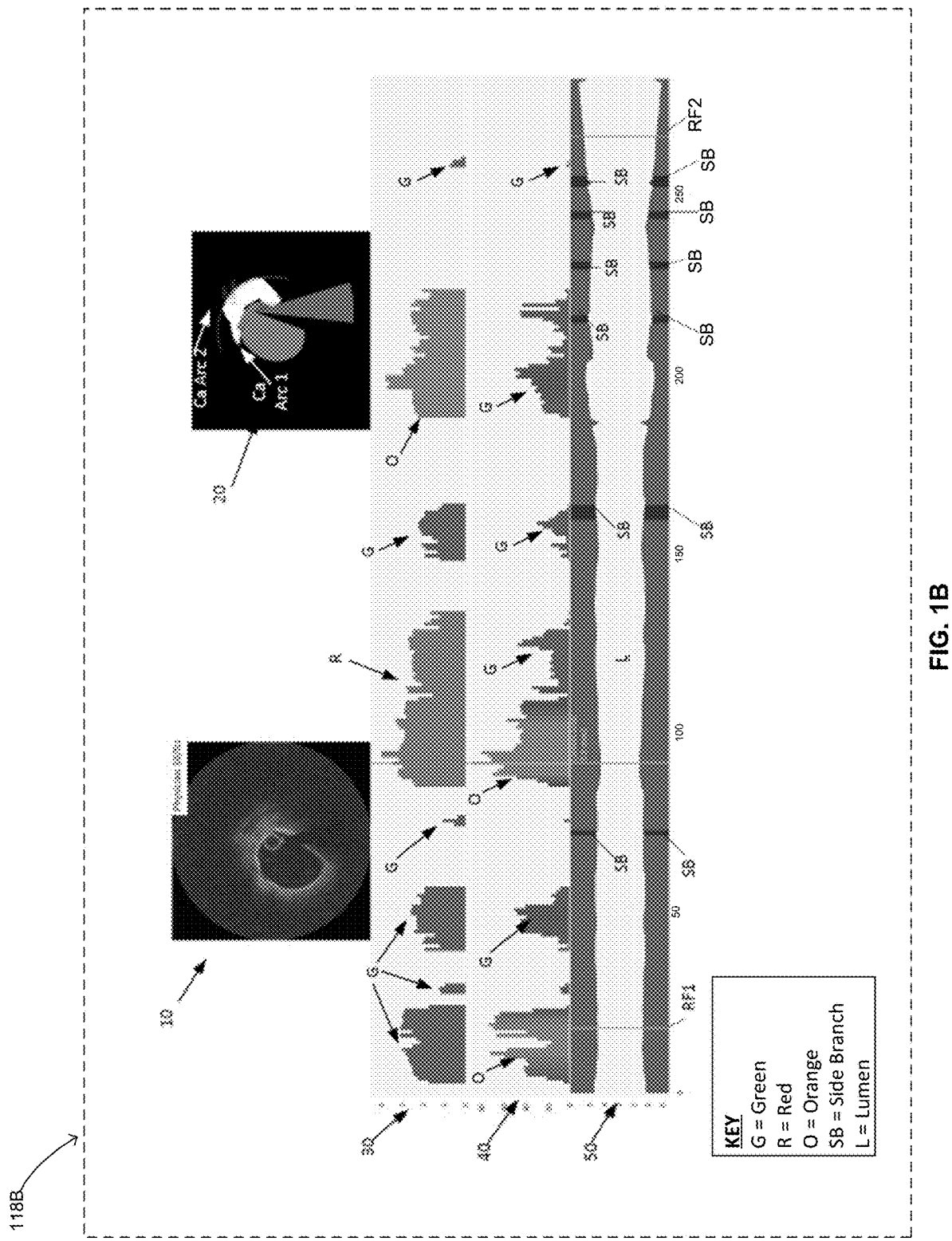
FIG. 1B is an example of a plurality of interface components according to aspects of the disclosure.

FIG. 1B illustrates various interface components that may be displayed on display 118B. As shown in FIG. 1B, the display 118B may include four different interface components. Chart 10 may display OCT imagery in Cartesian coordinates at a single frame. As shown, chart 10 may display frame 92 overlaid with the detected elliptical lumen edge. Chart 20 may display tissue characterization for the same frame, frame 92, in lumen-centered Cartesian coordinates. The lumen may be displayed in gray, guidewire shadow may be dark gray, media in red, and calcium in white. In this example, frame 92 does not include any detected visible media. The display may show each of these features in different colors based on the type of display. For example, if the display is black and white, the features may be displayed in greyscale. In examples where the display is a color display, the features may be displayed in any predetermined or user-preferred color. Charts 10, 20 may show the angular extent and thickness of the calcium at frame 92. For example, chart 20 may indicate the angular extent and thickness in arcs "Ca Arc 1" and "Ca Arc 2."

Charts 30, 40 may display longitudinal data, with frame numbers on the x-axis and per-frame measures on the y-axis. Chart 50 may display a longitudinal view of lumen area as well as highlighting side branches SB. Charts 30, 40, 50 may be aligned such that a frame in chart 50 is visually below or in line with the same frame in charts 30, 40. Chary 50 may include an indication of a first reference frame "RF1," second reference frame "RF2," and GUI reference frame. The references frames may be chosen based on a machine learning model or by the user. The references frames RF1, RF2, GUI may be used for calculations and/or to show various other views on screen when selected.

Chart 30 may illustrate the calcification risk score as developed by Cardiovascular Research Foundation ("CRF") in Fujino, A., et al., A New Optical Coherence Tomography-based Calcium Scoring System to Predict Stent Underexpansion, 13 (18) EUROINTERVENTION e2182-e2189 (Apr. 6, 2018). Chart 30 may be determined by identifying, for each frame, the largest calcium deposit and measuring its total radial area in degree•mm.

According to some examples, thickness (mm) may be limited to no more than 1 mm, as OCT tissue penetration and, in some examples, calcium detection accuracy, may be limited after 1 mm Additionally or alternatively, the thickness may be limited between 0.25 mm to 1.5 mm, 0.5 mm and 1.25 mm, 0.5 mm and 1.6 mm, 0.5 mm and 2.0 mm, depending on calcium detection accuracy. In some examples, length of the calcium may be limited between 0.1 mm and 10 mm, 0.1 mm and 7.5 mm, 0.1 mm and 5 mm, 0.5 mm and 5 mm, depending on calcium detection accuracy. The arc of calcium may be limited between 0 degrees and 360 degrees, 0 degrees and 270 degrees, 0 degrees and 180 degrees, depending on calcium detection accuracy.

The total radial area may be measured based on a combination of any of the ranges provided above and herein. For example the total radial area may be measured by any one of the following combinations of calcium thicknesses, calcium lengths and arcs of calcium: a calcium thickness between 0.25 mm to 1.5 mm, a calcium length between 0.1 mm and 10 mm, and a calcium arc between 0 degrees and 360 degrees; a calcium thickness between 0.25 mm to 1.5 mm, a calcium length between 0.1 mm and 10 mm, and a calcium arc between 0 degrees and 270 degrees; a calcium thickness between 0.25 mm to 1.5 mm, a calcium length between 0.1 mm and 10 mm, and a calcium arc between 0 degrees and 180 degrees; a calcium thickness between 0.25 mm to 1.5 mm, a calcium length between 0.1 mm and 7.5 mm, and a calcium arc between 0 degrees and 360 degrees; a calcium thickness between 0.25 mm to 1.5 mm, a calcium length between 0.1 mm and 7.5 mm, and a calcium arc between 0 degrees and 270 degrees; a calcium thickness between 0.25 mm to 1.5 mm, a calcium length between 0.1 mm and 7.5 mm, and a calcium arc between 0 degrees and 180 degrees; a calcium thickness between 0.25 mm to 1.5 mm, a calcium length between 0.1 mm and 5 mm, and a calcium arc between 0 degrees and 360 degrees; a calcium thickness between 0.25 mm to 1.5 mm, a calcium length between 0.1 mm and 5 mm, and a calcium arc between 0 degrees and 270 degrees; a calcium thickness between 0.25 mm to 1.5 mm, a calcium length between 0.1 mm and 5 mm, and a calcium arc between 0 degrees and 180 degrees; a calcium thickness between 0.25 mm to 1.5 mm, a calcium length between 0.5 mm and 5 mm, and a calcium arc between 0 degrees and 360 degrees; a calcium thickness between 0.25 mm to 1.5 mm, a calcium length between 0.5 mm and 5 mm, and a calcium arc between 0 degrees and 270 degrees; a calcium thickness between 0.25 mm to 1.5 mm, a calcium length between 0.5 mm and 5 mm, and a calcium arc between 0 degrees and 180 degrees; a calcium thickness between 0.5 mm and 1.25 mm, a calcium length between 0.1 mm and 10 mm, and a calcium arc between 0 degrees and 360 degrees; a calcium thickness between 0.5 mm and 1.25 mm, a calcium length between 0.1 mm and 10 mm, and a calcium arc between 0 degrees and 270 degrees; a calcium thickness between 0.5 mm and 1.25 mm, a calcium length between 0.1 mm and 10 mm, and a calcium arc between 0 degrees and 180 degrees; a calcium thickness between 0.5 mm and 1.25 mm, a calcium length between 0.1 mm and 7.5 mm, and a calcium arc between 0 degrees and 360 degrees; a calcium thickness between 0.5 mm and 1.25 mm, a calcium length between 0.1 mm and 7.5 mm, and a calcium arc between 0 degrees and 270 degrees; a calcium thickness between 0.5 mm and 1.25 mm, a calcium length between 0.1 mm and 7.5 mm, and a calcium arc between 0 degrees and 180 degrees; a calcium thickness between 0.5 mm and 1.25 mm, a calcium length between 0.1 mm and 7.5 mm; a calcium thickness between 0.5 mm and 1.25 mm, a calcium length between 0.1 mm and 5 mm, and a calcium arc between 0 degrees and 360 degrees; a calcium thickness between 0.5 mm and 1.25 mm, a calcium length between 0.1 mm and 5 mm, and a calcium arc between 0 degrees and 270 degrees; a calcium thickness between 0.5 mm and 1.25 mm, a calcium length between 0.1 mm and 5 mm, and a calcium arc between 0 degrees and 180 degrees; a calcium thickness between 0.5 mm and 1.25 mm, a calcium length between 0.1 mm and 5 mm; a calcium thickness between 0.5 mm and 1.25 mm, a calcium length between 0.5 mm and 5 mm, and a calcium arc between 0 degrees and 360 degrees; a calcium thickness between 0.5 mm and 1.25 mm, a calcium length between 0.5 mm and 5 mm, and a calcium arc between 0 degrees and 270 degrees; a calcium thickness between 0.5 mm and 1.25 mm, a calcium length between 0.5 mm and 5 mm, and a calcium arc between 0 degrees and 180 degrees; a calcium thickness between 0.5 mm and 1.6 mm, a calcium length between 0.1 mm and 10 mm, and a calcium arc between 0 degrees and 360 degrees; a calcium thickness between 0.5 mm and 1.6 mm, a calcium length between 0.1 mm and 10 mm, and a calcium arc between 0 degrees and 270 degrees; a calcium thickness between 0.5 mm and 1.6 mm, a calcium length between 0.1 mm and 10 mm, and a calcium arc between 0 degrees and 180 degrees; a calcium thickness between 0.5 mm and 1.6 mm, a calcium length between 0.1 mm and 7.5 mm, and a calcium arc between 0 degrees and 360 degrees; a calcium thickness between 0.5 mm and 1.6 mm, a calcium length between 0.1 mm and 7.5 mm, and a calcium arc between 0 degrees and 270 degrees; a calcium thickness between 0.5 mm and 1.6 mm, a calcium length between 0.1 mm and 7.5 mm, and a calcium arc between 0 degrees and 180 degrees; a calcium thickness between 0.5 mm and 1.6 mm, a calcium length between 0.1 mm and 5 mm, and a calcium arc between 0 degrees and 360 degrees; a calcium thickness between 0.5 mm and 1.6 mm, a calcium length between 0.1 mm and 5 mm, and a calcium arc between 0 degrees and 270 degrees; a calcium thickness between 0.5 mm and 1.6 mm, a calcium length between 0.1 mm and 5 mm, and a calcium arc between 0 degrees and 180 degrees; a calcium thickness between 0.5 mm and 1.6 mm, a calcium length between 0.5 mm and 5 mm, and a calcium arc between 0 degrees and 360 degrees; a calcium thickness between 0.5 mm and 1.6 mm, a calcium length between 0.5 mm and 5 mm, and a calcium arc between 0 degrees and 270 degrees; a calcium thickness between 0.5 mm and 1.6 mm, a calcium length between 0.5 mm and 5 mm, and a calcium arc between 0 degrees and 180 degrees; a calcium thickness between 0.5 mm and 2.0 mm, a calcium length between 0.1 mm and 10 mm, and a calcium arc between 0 degrees and 360 degrees; a calcium thickness between 0.5 mm and 2.0 mm, a calcium length between 0.1 mm and 10 mm, and a calcium arc between 0 degrees and 270 degrees; a calcium thickness between 0.5 mm and 2.0 mm, a calcium length between 0.1 mm and 10 mm, and a calcium arc between 0 degrees and 180 degrees; a calcium thickness between 0.5 mm and 2.0 mm, a calcium length between 0.1 mm and 7.5 mm, and a calcium arc between 0 degrees and 360 degrees; a calcium thickness between 0.5 mm and 2.0 mm, a calcium length between 0.1 mm and 7.5 mm, and a calcium arc between 0 degrees and 270 degrees; a calcium thickness between 0.5 mm and 2.0 mm, a calcium length between 0.1 mm and 7.5 mm, and a calcium arc between 0 degrees and 180 degrees; a calcium thickness between 0.5 mm and 2.0 mm, a calcium length between 0.1 mm and 5 mm, and a calcium arc between 0 degrees and 360 degrees; a calcium thickness between 0.5 mm and 2.0 mm, a calcium length between 0.1 mm and 5 mm, and a calcium arc between 0 degrees and 270 degrees; a calcium thickness between 0.5 mm and 2.0 mm, a calcium length between 0.1 mm and 5 mm, and a calcium arc between 0 degrees and 180 degrees; a calcium thickness between 0.5 mm and 2.0 mm, a calcium length between 0.5 mm and 5 mm, and a calcium arc between 0 degrees and 360 degrees; a calcium thickness between 0.5 mm and 2.0 mm, a calcium length between 0.5 mm and 5 mm, and a calcium arc between 0 degrees and 270 degrees; a calcium thickness between 0.5 mm and 2.0 mm, a calcium length between 0.5 mm and 5 mm, and a calcium arc between 0 degrees and 180 degrees.

This calcium radial area becomes the height of the bars displayed in the chart and can relate to the stent under-expansion risk at each frame. The color of the bars in chart 40, identified by "R," "O," and "G," may correlate to the average radial area in a 25 frame (5 mm) longitudinal window. Chart 40 may provide an informational view of the cumulative risk posed by adjacent frames of heavy calcium. For example, chart 40 may provide an additional or alternative way of showing the calcium burden. The colors used in chart 30 may correspond to the colors used in chart 30. Bars in chart 30 may be fully red when they reach a sliding-window radial area of 180°×0.5 mm=90 degree-mm.

Figure 2A:
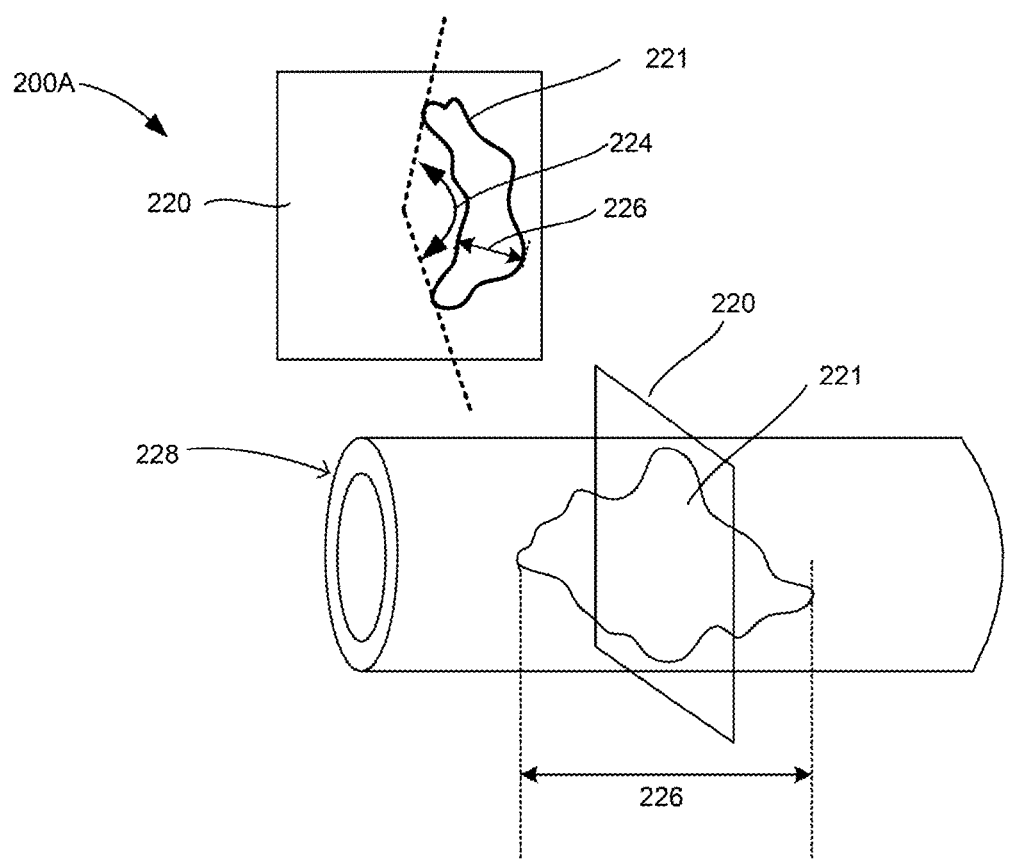
FIGS. 2A is an existing example scoring methodology.
Figure 2B:
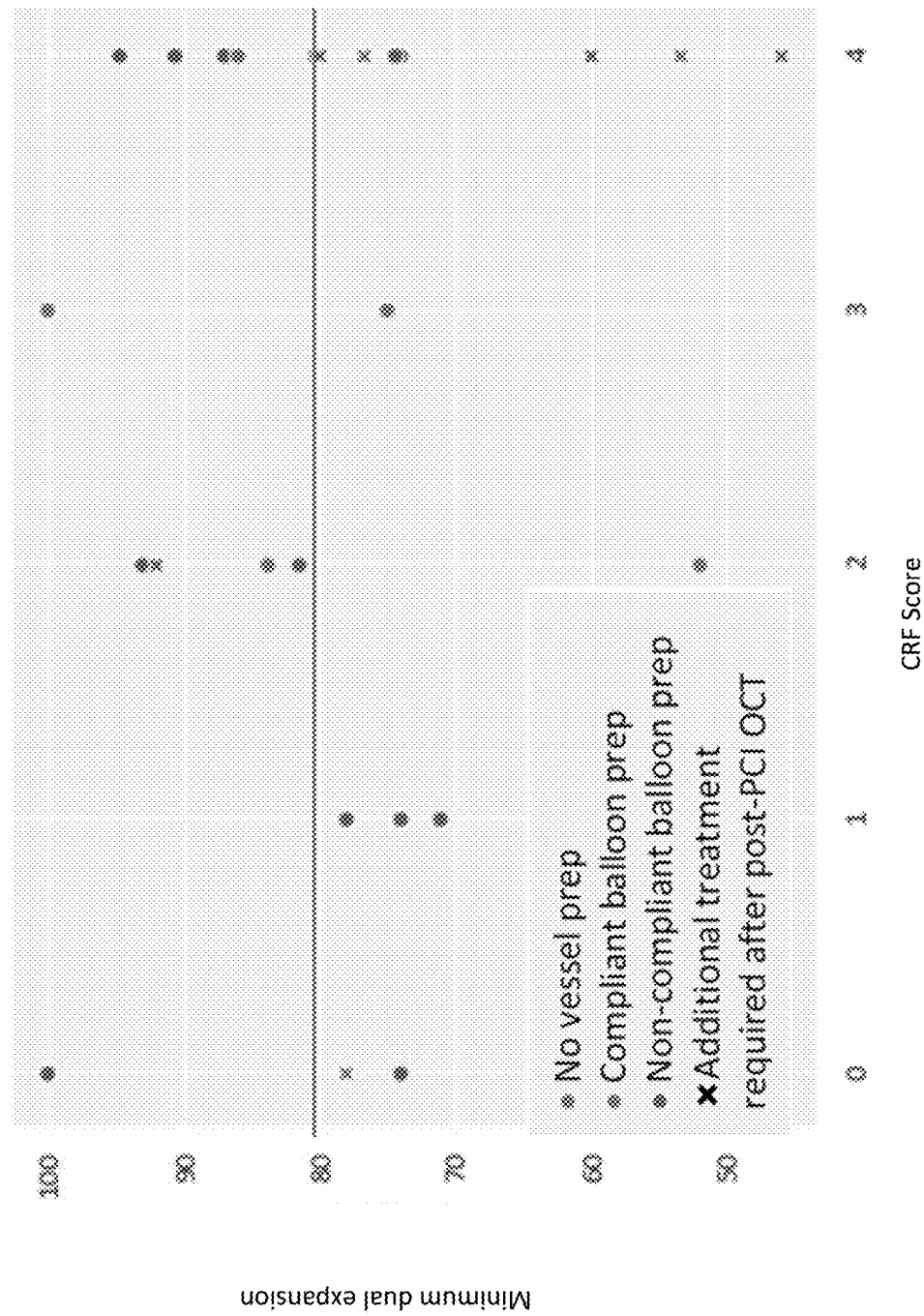
FIG. 2B is an example graphical representation of the scoring methodology of FIG. 2A.
Figure 2C:
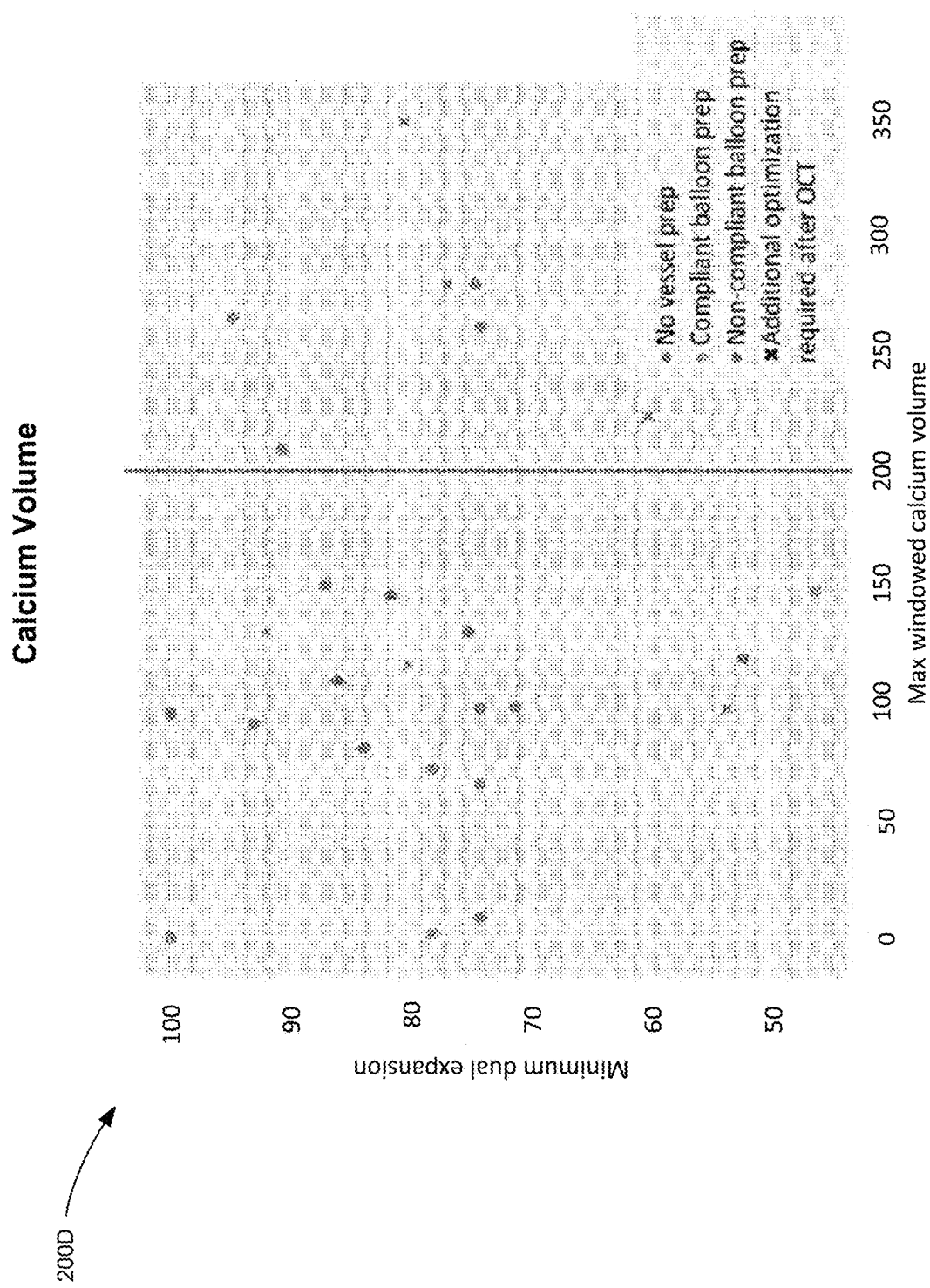
FIG. 2C is an example graphical representation of the scoring methodology of FIG. 2B according to aspects of the disclosure.

FIGS. 2A-2C illustrate examples of how the frames may be scored, analyzed and/or displayed based on chart 30. FIG. 2A is referenced from Fujino, A., et al.

FIG. 2A includes a blood vessel segment 228 and a cross-sectional image corresponding to a frame 220 of image data. A maximum angle 222 and/or maximum thickness 224 of calcium within frame 220 may be determined. Additionally or alternatively, the length 226 of the calcium 221 may be determined based on a longitudinal representation of the blood vessel 228.

Each frame may be analyzed. For each frame, one or more of the following may be calculated:

1. If the largest calcium arc in the frame is greater than 180°, the frame score receives 2 points, otherwise, it receives 2*arc_degrees/180 points;
2. If the largest calcium arc in the frame has a thickness greater than 0.5 mm, then the frame receives 1 additional point, otherwise, it receives 1*thickness_mm/0.5;

3. If the length of the calcium deposit is greater than 5 mm (approximately 25 frames), then each frame in the deposit receives an addition 1 point, otherwise, they receive 1*length_mm/5;
4. If the multi-frame calcium deposit receives a calcium score of 4, then all the area displayed for that deposit is colored red. Scores of 2 and 3 are orange, and scores of 1 are green.

The OCT-based calcium score based on the one or more calculations described with respect to FIG. 2A. For example, the OCT-based calcium score may be a value between zero (0) and four (4) points. The score may be based on the maximum calcium angle, the maximum calcium thickness, and/or the calcium length. In examples where the maximum calcium angle is less than or equal to 180 degrees, the score may be zero points. In examples where the maximum calcium angle is greater than 180 degrees, the score may be two points. In examples where the maximum calcium thickness is less than or equal to 0.5 mm, the score may be zero points. In examples where the maximum calcium thickness is greater than 0.5 mm, the score may be one point. In examples where the calcium length is less than or equal to 5.0 mm, the score may be zero points. In examples where the calcium length is greater than 5.0 mm, the score may be one point. A total score may be determined based on the individual scores for one or more of the maximum calcium angle, maximum calcium thickness, and calcium length. The actual measurements and/or thresholds may change based on machine learning models. The machine learning models may determine coefficients for these factors as they relate to stent expansion though case study inputs. The evaluation and scoring may be completed by the physician. However, the systems and methods described herein may automate the evaluation and scoring. The computing device 112 may use the charts of FIG. 1B, such as chart 30, to apply the evaluation criteria and provide an automated score.

According to some examples, the calcium score may be calculated using a sliding window measure. A sliding window measure may include a window or range around each given point of the line. The window may slide down the line as each point is recalculated. According to some examples, for every frame, the risk score may be recalculated by accounting for the full length of the calcified plaque. In some examples, the risk score may, additionally or alternatively, be recalculated based on the calcium thickness and/or calcium angle at each particular frame. The sliding window measure may be calculated by multiplying the calcium length in mm by the calcium thickness in mm and by the calcium angle in degrees. For example, the equation may be:

Sliding Window Measure=Calcium Length×Calcium Thickness×Calcium Angle

The radial area may be determined by multiplying the calcium thickness by the calcium angle. The sum of the radial are may be measured in a 5 mm window. However, a 5 mm window is merely one example as the window may be more or less than 5 mm and, therefore, is not meant to be limiting.

FIG. 2B illustrates a graphical representation 200C of example calculated OCT-based scores. Lesions with a CRF score of 4 may indicate that the stent is not under-expanded. According to some examples, lesions with a CRF score of 4 may not be under-expanding (<80%) any more frequently than low-scoring cases: (50±16% vs 53±12%). In some examples, lesions with a CRF score of 4 may require additional optimization 50% of the time (vs 13% in low-scoring cases).

FIG. 2C illustrates a graphical representation 200D of examples calculate calcium volume. There may be a negative correlation between calcium volume and stent expansion. For example, approximately 67% of cases with high calcium volume (>200 deg×mm$^2$) may have under-expanded stents (<80%) vs 48%) as compared to cases with low calcium volume. According to some examples, approximately 50% of high calcium volume cases may require additional optimization after OCT as compared to 24% of low calcium volume cases.

FIGS. 2C and 2D may illustrate that the windowed calcium volume may better estimate the stent under-expansion risk than the CRF score.

Figure 3:
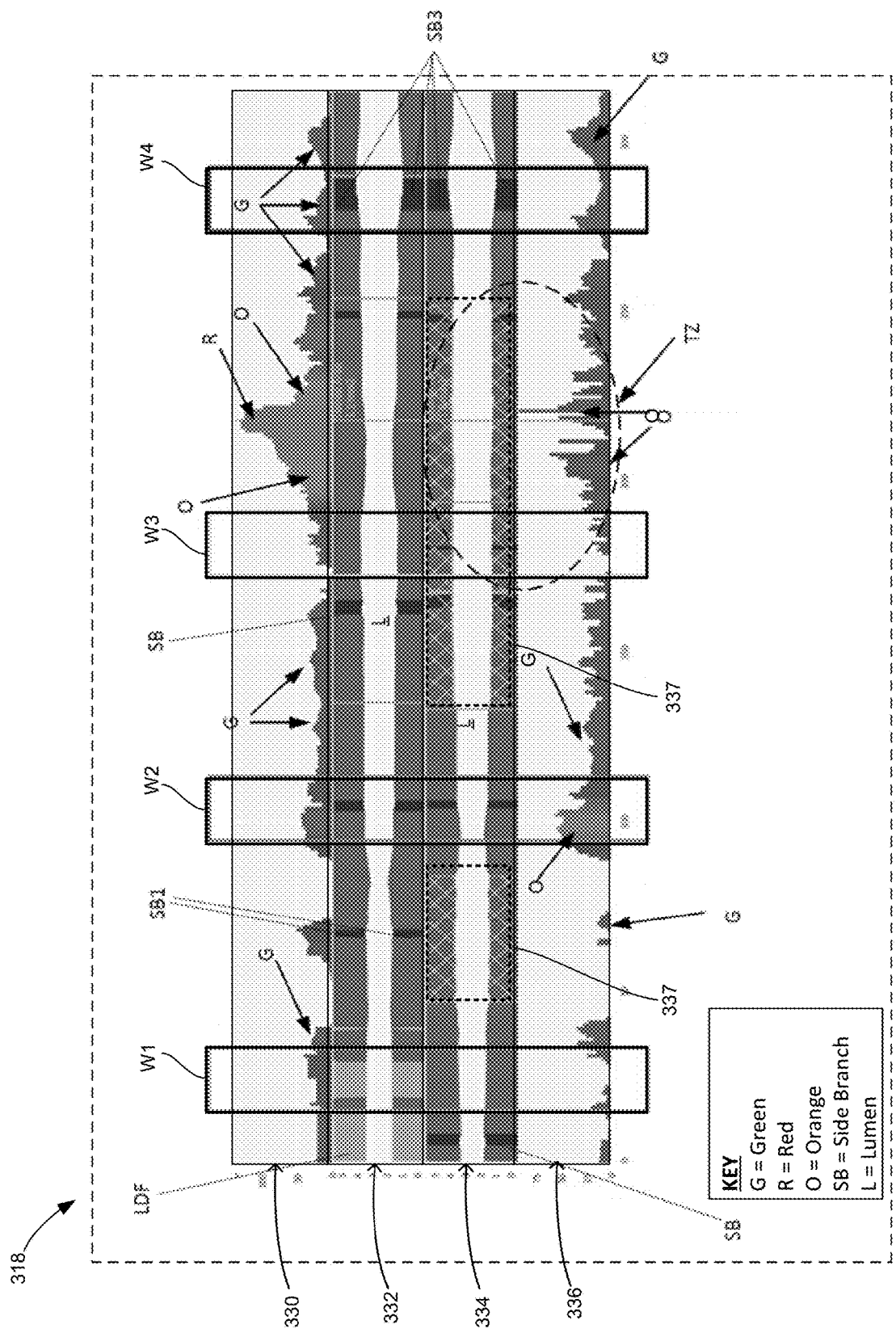
FIG. 3 is an example display according to aspects of the disclosure.

FIG. 3 illustrates an example output for display. OCT pullback images from before and after stent deployment may be aligned to provide information correlating calcium burden to stent expansion. A correlation between calcium burden and stent expansion may allow a physician or user to assess the role of calcium burden in stent expansion. Display 318 may include charts 330, 332, 334, 336. Chart 330 may display data or frames pertaining to pre-percutaneous coronary intervention ("PCI") PCI calcium, chart 332 may display data or frames pertaining to pre-PCI lumen, chart 334 may display data or frames pertaining to post-PCI lumen, and chart 336 may display data or frames pertaining to post-PCI calcium. The pre-PCI calcium and lumen view, charts 330, 332, respectively, may be displayed adjacent to the calcium and lumen views for the post-PCI pullback, charts 334, 336, respectively. The post-PCI pullback views may include the stented regions 337.

Display 318, as shown, includes W1, W2, W3, W4. Each window W1, W2, W3, W4 may have a different purpose or provide a different indication of a detected feature. According to some examples, the windows may be output for display. In other examples, the windows are not output for display.

Window W1 may indicate a region of the blood vessel having the flexibility to stretch the pullback in order to maximize alignment. Window W2 may indicate a region of the blood vessel that includes points for lining up calcium. Window W3 may indicate a region of the blood vessel that includes points for lining up the stent. Window W4 may indicate a region of the blood vessel that includes points for lining up side-branches. While the windows are shown in FIG. 3 this is merely to assist in explaining the output and, therefore, may not be output for display.

The display may include an indication of a region of the blood vessel where the degree of pre-treatment, such as an angioplasty with a balloon prior to stenting, may impact a reduction in the impact of calcium burden.

The system may use the Needleman-Wunsch algorithm or a modified version of the Needleman-Wunsch algorithm for scoring in an attempt to line up calcium, pre-existing stents, side branches, and relative lumen area. According to some examples, a candidate alignment gets points for having at least one of the following:
1. A similar number of arc degrees with calcium in a frame: min(pre, post)/max(pre, post,) 60°;
2. A similar total diameter side branch in a frame: min(pre, post)/max(pre, post, 0.5 mm);
3. A similar relative lumen area in a frame: min(rla_pre, rla_post)/max(rla_pre, rla_post, 0.1), where rla_pre and rla_post are the relative lumen area in a frame, calculated as:

rla_pre[f]=(lumen area at f)/(lumen area at F)

rla_post[f]=(lumen area at f)/(lumen area at F)

where F is the proximal reference frame in the post-PCI pullback and F' is the pre-PCI frame corresponding to F in this candidate alignment.

The algorithm may not match calcium or lumen areas in stented regions, as the act of stenting may change both the calcium and lumen profiles. According to some examples, not matching the calcium or lumen in stented regions may be compensated for by using an error range or other statistical corrections.

Figure 4:
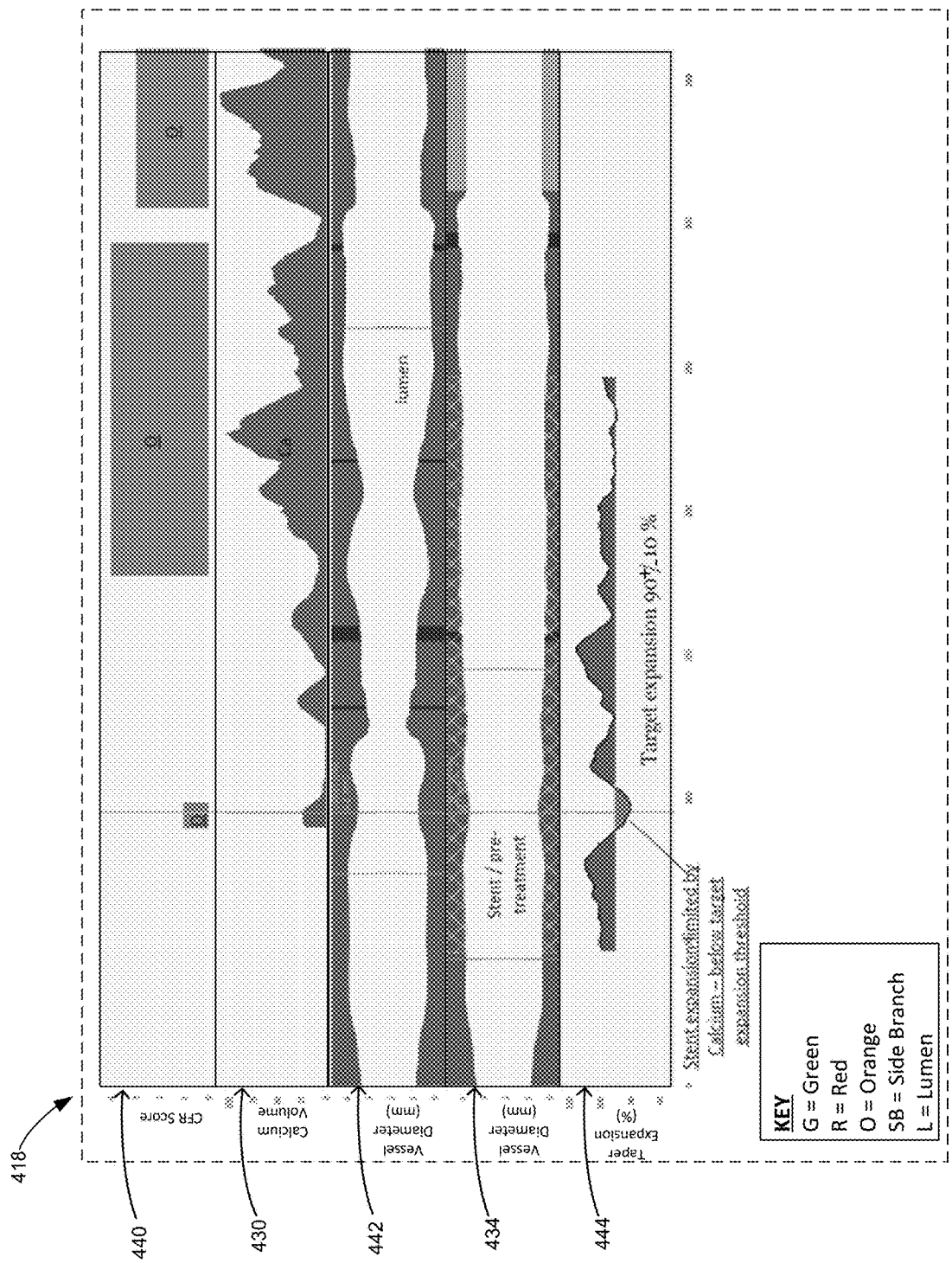
FIG. 4 is an example display according to aspects of the disclosure.

FIG. 4 illustrates an example display. The display 418 may include chart 440 illustrating the CFR score of the blood vessel, chart 430 illustrating the pre-PCI calcium of the blood vessel, chart 442 illustrating a 2D longitudinal representation of the blood vessel, chart 434 illustrating the post-PCI lumen of the blood vessel, and chart 444 illustrating the taper expansion. According to some examples, the taper expansion may be determined by recalculating the appropriate reference area for each frame based on the natural taper from the proximal to distal end of the blood vessel as the side branches divert blood flow. Chart 430 may use the sliding window measure described above. Additionally or alternatively chart 430 may be based on the windowed-calcium volume plotted in chart 40. Chart 430 may be similar to the chart 40, shown in FIG. 1B. Chart 442 may be similar to chart 50, shown in FIG. 1B. Chart 434 may be similar to chart 50 of FIG. 1B but, instead, may only display the same region of the blood vessel after the stent has been deployed.

According to some examples, the display may indicate or identify a region of detected calcium. The identified region of detected calcium may represent a negative correlation with stent expansion by limiting amount of stent expansion as shown by local minima in stent expansion threshold plot. Chart 444, which may illustrate taper expansion, may show changes to lumen profile as calculated using reference frames at either ends, proximal and/or distal, of pullback.

While not shown on charts 440, 430, 442, 434, 444 of display 418, red regions may indicate a high or increased calcium burden that may require consideration when stenting the blood vessel. Green regions may indicate a decreased or low calcium burden. In some examples, orange regions "O" may indicate intermediate regions of calcium burden where the impact of the calcium burden may warrant further analysis or other views using cross-sectional, l-mode, and other intravascular views and analysis. It should be understood that this is merely one example, and that in other examples risks may be color-coded using a different color scheme.

Stent Underexpansion

Figure 5:
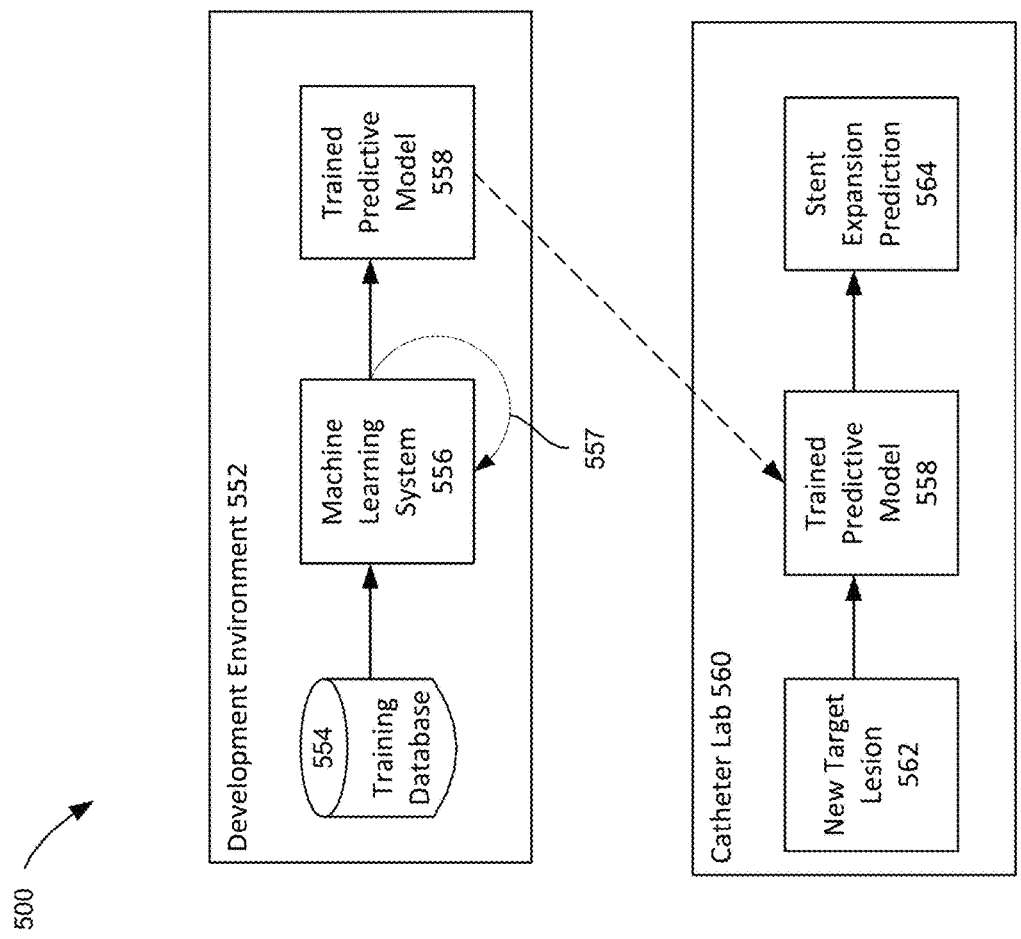
FIG. 5 is an example system according to aspects of the disclosure.

The calcium burden described above and herein may be used to estimate stent under-expansion risk. Stent under-expansion risk may be estimated using a trained machine learning ("ML") model. Each training example may be a case from a clinical trial and/or from the field. The ML model may compare pre-PCI information and post-PCI outcome for each case. The ML model estimate may be used to provide a physician or end-user a quantitative assessment of the under-expansion risk FIG. 5 illustrates an example system 500 that uses data from past PCIs to predict stent under-expansion risk for future patients. The system 500 may include a development environment 552 and a catheter lab 560. While shown as a catheter lab 560, the catheter lab 560 may be any location in which a physician inserts or implants a stent into a patient. For example, the catheter lab may be at a hospital, an outpatient surgical location, etc. Thus, identifying the location as catheter lab 560 is merely one example and is not intended to be limiting.

The development center 552 may include a training database 5545, a machine learning system 556, and a trained predictive model 558A. The training database may contain PCI information at multiple levels. For example, the training database 554 may include coarse statistics from published clinical studies, records and imagery on individual PCIs from clinical trials, and data on PCIs collected in the field. These data may be in the form of input-output pairs, where the input for a case is all the information observable before the target vessel is prepared and stent deployed, and the output is the resulting stent expansion and other outcomes (complications, re-hospitalization, TVR, etc.). The input-output pairs may be one or more image frames. According to some examples, the input may be a plurality of images of the target vessel before the target vessel is prepared and the output may be a plurality of images of the target vessel after stent expansion, etc. The input plurality of images may correspond to the output plurality of images such that a first frame of the input plurality of images is from the same location within the target vessel as the first frame of the output plurality of images.

The machine learning system 556 may learn or model the relationship between these inputs and outputs. For example, the machine learning system 556 may detect different values from each of the plurality of input and output images. The values may include, but are not limited to, the calcium angle, the maximum thickness, the percentage of stent expansion, etc. for each of the plurality of input and output images. Each of these values may be used to later predict stent under-expansion risk levels. According to some examples, the machine learning system 556 may learn the relationship by adjusting internal parameters to minimize error in its output predictions.

According to some examples, a linear model such as a logistic regression may adjust internal parameters that are multiplicative weights placed on each predictor attribute. For example, one model may be:

$$\text{Expansion}=(w1)*(\text{calcium})+(w0)$$

Expansion may be the stent expansion percentage that is to be predicted. Calcium may be the maximum windowed calcium volume. "W1" and "w0" may be a numerical value that the algorithm may adjust to best fit the training data.

In some examples, the machine learning system may learn any number of decision trees such that its internal parameters may be the rules governing each tree. In one example, machine learning system may determine that when the calcium volume is less than 0.3, good expansion may be predicted.

In some examples, when the machine learning system 556 adjust model parameters to minimize prediction error, the machine learning system 556 may re-run 557 the data to create an additional model.

The models created by the machine learning system 556 may be a trained predictive model 558. The trained predictive model 558 may predict the stent under-expansion risk. The trained predictive model 558 may be sent to the catheter lab 560. According to some examples, the trained predictive model 558 may be shared via a network. In the catheter lab 560, the trained predictive model 558 may use and/or take information about a new target lesion 562 and generate stent expansion predictions 564 to support the physician in refining their intervention strategy. The stent expansion prediction 564 may include a stent under-expansion risk.

Figure 6:
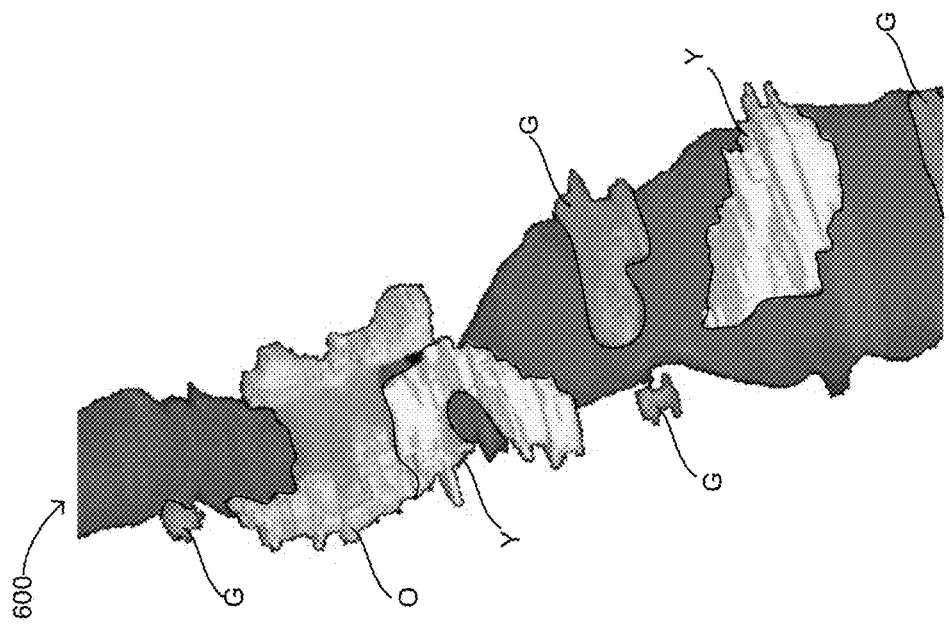
FIG. 6 is an example blood vessel according to aspects of the disclosure.

FIG. 6 illustrates example lesions in a blood vessel 600 that may be targeted. Lesions "Y" may be thick, eccentric calcium deposits. Lesions "O" may be a thick circumferential calcium deposit. Lesions "G" may be thin, eccentric calcium deposits. According to some examples, the lesions "Y" may be color coded as yellow, lesions "O" may be color coded orange, and lesions "G" may be color coded green on the display.

According to some examples, the lesion calcification may be eccentric, where the calcification is on just one side of the vessel, or circumferential, such that the calcification wraps around the inner circumference of the vessel. Circumferential calcium may pose the greatest risk to stent expansion, as it may prevent the stent balloon from expanding in all directions. Not all calcium may resist stent expansion. Some calcium may be thin enough that the stent may expand through it. Some calcium may not form a large enough arc around the vessel, allowing the stent to break through the calcium at one or more hinge points. Some may be more of a mixed plaque type, having calcium deposits in a matrix of lipid and/or fiber.

Figure 7:
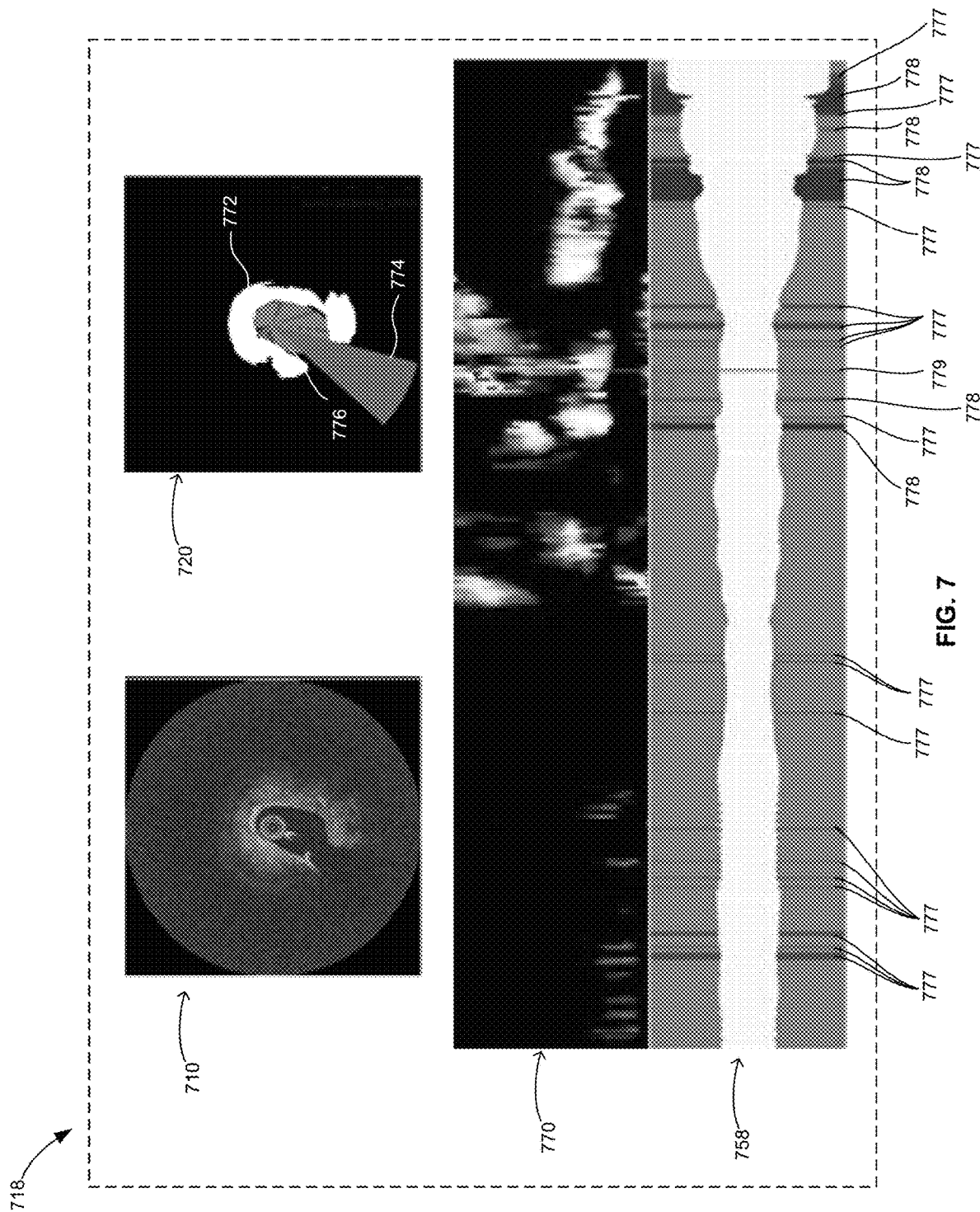
FIG. 7 is an example of a plurality of interface components according to aspects of the disclosure.

FIG. 7 illustrates an example of a plurality of interface components that may be output to display 718. The plurality of interface components may be used to determine lesions in a blood vessel. Frame 710 may be an OCT image of a single cross-section frame of a coronary artery with a calcified lesion. Frame 720 may be a tissue characterization of frame 710 including the calcium 772, guidewire shadow 774, and the identified lumen 776. Output 770 may be an enface projection of calcium. In some examples, each pixel's horizontal position may indicate the longitudinal frame location. Additionally or alternatively, each vertical position may indicate the angular position around the lumen center. The pixel intensity, shown in greyscale, may indicate the calcium thickness at that frame and arc. Output 758 may indicate lumen diameter across the pullback. Indicia 777 may indicate a frame where lumen diameter estimate may have larger errors. Indicia 778 may indicate a detected side branch. Indicia 779 may indicate the frame displayed in the cross-sectional frames 710, 720.

For the vessel region to be stented, tissue characterization may be generated for that region of the OCT pullback. Pixels in the frames may be identified as calcium. From the pixels identified as calcium, the thickness of the calcium may be measured at each radial angle around the vessel lumen center. Frame 720 may include 360 degrees of calcium that is greater than 0.0 mm thick. According to some examples, frame 720 may include 45 degrees of calcium that is greater than 0.8 mm thick and 0 degrees of calcium that is greater than 1.0 mm thick. Frame 720 may be used as the input feature vector in the machine learning model. According to some examples, six thickness thresholds may be used when measuring the largest contiguous arc of calcium at those thresholds. The thresholds may be, for example, 0.0 mm, 0.2 mm, 0.4 mm, 0.6 mm, 0.8 mm, and 1 mm. However, the thresholds may be any value in mm, such as 0.1, 0.25, etc. Thus, thresholds 0.0 mm, 0.2 mm, 0.4 mm, 0.6 mm, 0.8 mm, and 1 mm are merely one example of the six thresholds and is not intended to be limiting. Additionally or alternatively, there may be four thresholds, five thresholds, eight thresholds, etc. and, therefore, the examples of six thresholds is not intended to be limiting to the number of thresholds that may be used.

Using the example thresholds 0.0 mm, 0.2 mm, 0.4 mm, 0.6 mm, 0.8 mm, and 1 mm with respect to frame 720, there may be 360 degrees of calcium that is greater than 0.0 mm thick but only 45 degrees of that calcium may be more than 0.8 mm thick and 0 degrees of that calcium may be greater than 1.0 mm thick. The vector of arcs for frame 720, based on the six thresholds may be 360, 360, 210, 180, 45, and 0.

In some examples, frame 720 may include 60 degrees of calcium that is greater than 0.6 mm thick and 15 degrees of calcium that is greater than 1.0 mm thick. Using the example thresholds with respect to frame 720, there may be 360 degrees of calcium that is greater than 0.0 mm thick but only 60 degrees of that calcium may be more than 0.5 mm thick and 15 degrees of that 60 degrees may be greater than 1.0 mm thick. The vector arcs for frame 720, based on the example thresholds, may be 360, 360, 60, 15, and 15.

According to some examples, frame 720 may include 365 degrees of calcium that is greater than 0.0 mm thick, 285 degrees of calcium that is greater than 0.75 mm thick and 30 degrees of that 285 degrees may be greater than 1.0 mm thick. Using the examples thresholds, the vector arcs for frame 720 may be 360, 360, 360, 360, 30, and 30.

Stent expansion may be influenced by calcium but also by a one or more other factors. For example, maximum balloon diameter, maximum balloon pressure, balloon/artery diameter ratio, coarse vessel location includes LAD, LCX, and RCA, lumen reference area, minimum lumen area, percentage of stenosis, stenosis divided by the maximum balloon pressure, minimum lumen area divided by the maximum balloon area, stent length, lumen eccentricity, calcium depth measured as the amount of tissue in mm between the lumen edge and the first pixel of calcium in the frame, etc. One or more of these factors may be used as input in the machine learning model.

Figure 8B:
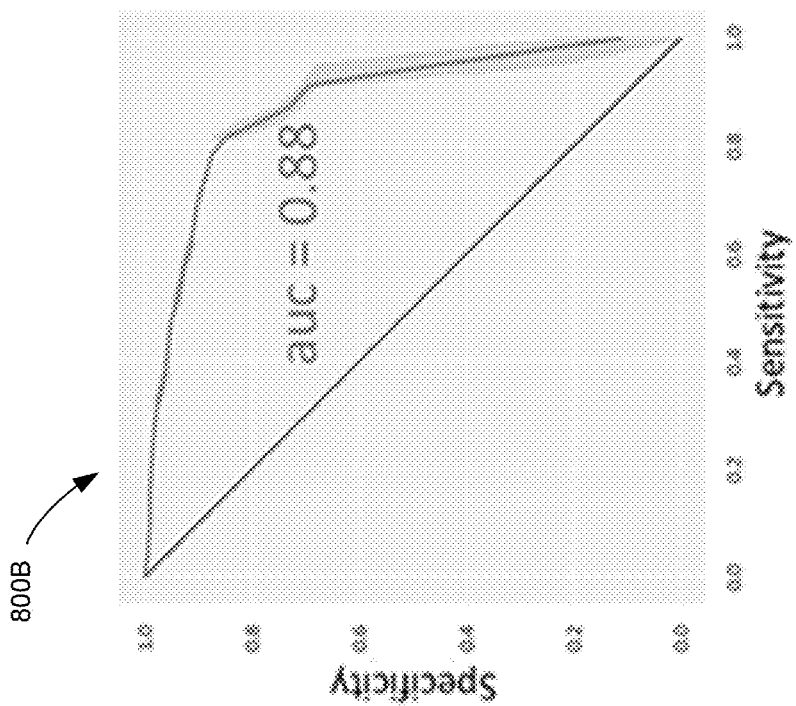
FIGS. 8A and 8B are example graphical representations of cross-validation results.
Figure 8A:
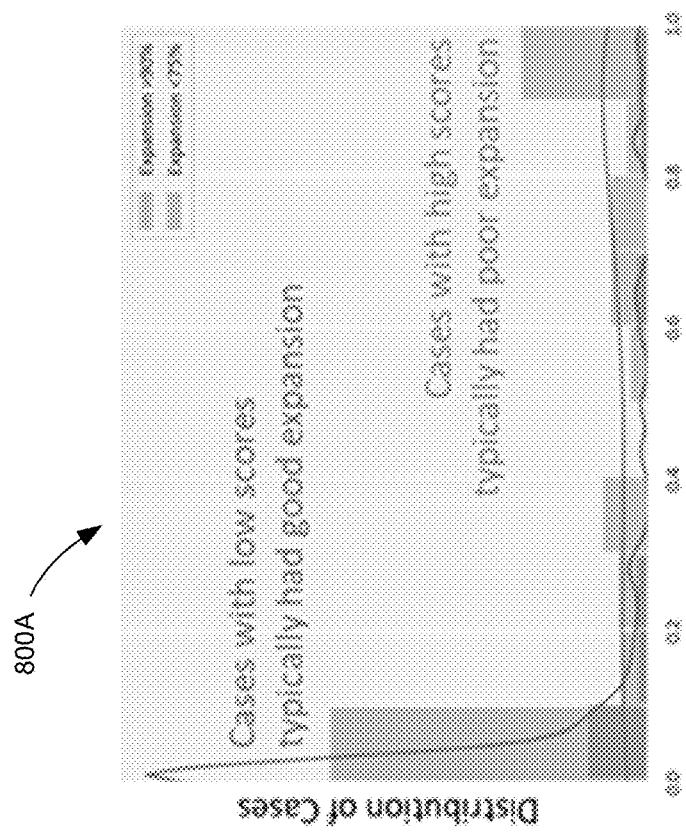

FIGS. 8A and 8B illustrate an example of cross-validation results for a machine learning model prediction of whether a stent expanded well or poorly. For this example, a stent expanded well if the stent had greater than 90% expansion and the stent expanded poorly if the stent had less than 70% expansion. According to some examples, a stent expanded well if the stent had greater than 85% expansion and the stent expanded poorly if the stent had less than 55% expansion. In some examples, a stent expanded well if the stent had greater than 87% expansion and the stent expanded poorly if the stent had less than 60% expansion.

As shown in FIG. 8A, cases with will expanded stents, for example those with an expansion rate greater than 90%, may receive a low risk estimate whereas cases with poorly expanded stents, for example those with an expansion rate less than 75%, may be found to have higher risk estimates.

FIG. 8B relates specificity and sensitivity at varying thresholds. Machine learning algorithms may predict either a number, such as a rate of expansion, or a class label, such as well expanded or poorly expanded. As shown, FIG. 8B may show the performance of a classifier when the algorithm produces a numeric score than just a label prediction. The classifier may be from an algorithm that is predicting a class label. Each point on the curve may represent the performance at a different decision-threshold. For example, at a score of 0.9 the sensitivity may be 0.9 and the specificity may be 0.7.

According to some examples, the risk assessment, or the stent under-expansion risk, may be displayed on the display or GUI as a probability. For example, there may be an indication on the display that the stent has an 80% chance of being poorly expanded. An 80% chance of being poorly expanded may, according to some examples, indicate a high risk of stent under-expansion.

Figure 9A:
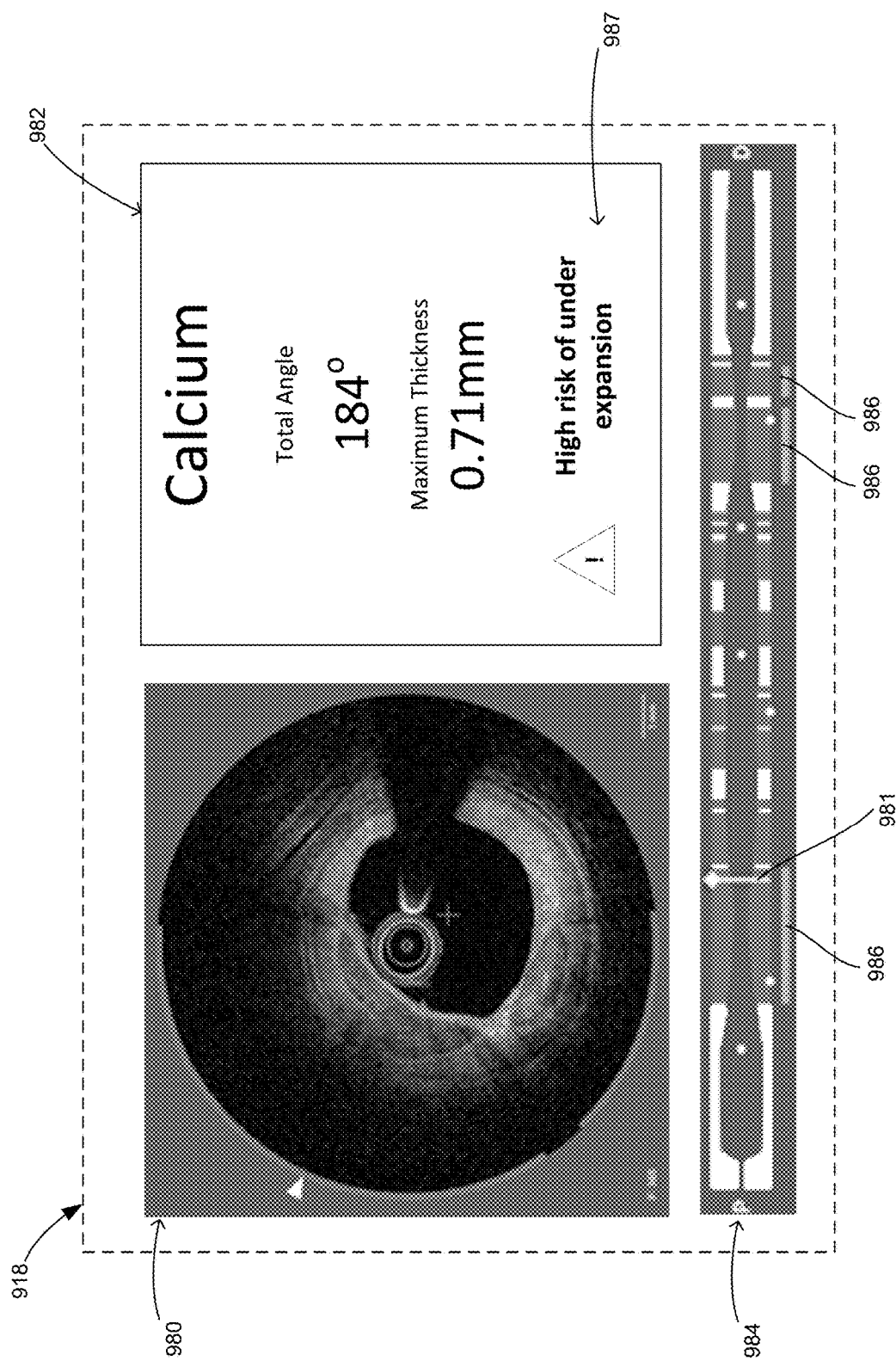
FIG. 9A is an example display according as aspects of the disclosure.

FIG. 9A illustrates an example display including a risk assessment. Display 918 may include a longitudinal representation 984 of the blood vessel, the selected frame 980 within the longitudinal representation 984, and an information display 982. The longitudinal representation 984 may include an indication or marker 981 identifying the selected frame 980. The information display may include the total angle of the calcium in the selected frame 980, the maximum thickness of the calcium in the selected frame 980, and the risk assessment 987.

The risk assessment 987 may include an indication or warning of the risk of stent under-expansion. The risk of stent under-expansion may be ranked from high to low. For example a high risk of stent under-expansion may indicate that there is a 75% or greater chance of under-expansion, a moderate risk of stent under-expansion may indicate that there is a 25% to 75% risk of stent under-expansion, and a low risk of stent under-expansion may indicate that there is less than a 25% chance of stent under-expansion. In some examples, a high risk may indicate that there is an 80% or greater chance of under-expansion, a moderate risk may indicate that there is a 35% to 80% risk of under-expansion, and a low risk may indicate that there is less than a 35% risk of under-expansion. Additionally or alternatively, a high risk may indicate that there is an 85% or greater chance of under-expansion, a moderate risk may indicate that there is a 40% to 85% risk of under-expansion, and a low risk may indicate that there is less than a 3540 risk of under-expansion. In other examples, a high risk may indicate that there is a 60% or greater chance of under-expansion, a moderate risk may indicate that there is a 25% to 60% risk of under-expansion, and a low risk may indicate that there is less than a 25% risk of under-expansion.

In examples where there is a high risk of stent under-expansion, the risk assessment 987 may include a warning symbol, as shown, or a stop sign. In examples where there is a low risk of stent under-expansion, the risk assessment 987 may include a green light, or an "OK" symbol, not shown. The risk assessment 987 may be color coded such that a high risk of stent under-expansion may be written in red to alert the physician whereas a low risk of stent under-expansion may be written in green to give the "OK" to the physician. While high risk may be associated with a red color and low risk may be associated with a green color, the risk assessment 987 may use any color system, including grey-scale.

The longitudinal view 984 may, additionally or alternatively, include a risk assessment 986. The longitudinal risk assessment 986 may be shown as an indication, such as a bar, on or below the longitudinal view. The longitudinal risk assessment 986 may be color coded such that one color means high risk and another color means low risk. The color coding of longitudinal risk assessment 986 may correspond to the color coding of risk assessment 987. For example, a red longitudinal risk assessment may be high risk and a green longitudinal risk assessment may be low risk. In some examples, there may be additional color risks, such as orange or yellow, which may be moderate risk or a risk that should be considered. According to some examples, individual frames within the longitudinal view 984 may be color coded or highlighted. The color coding and/or highlighting may be similar to the color code used for the longitudinal risk assessment 986.

Figure 9B:
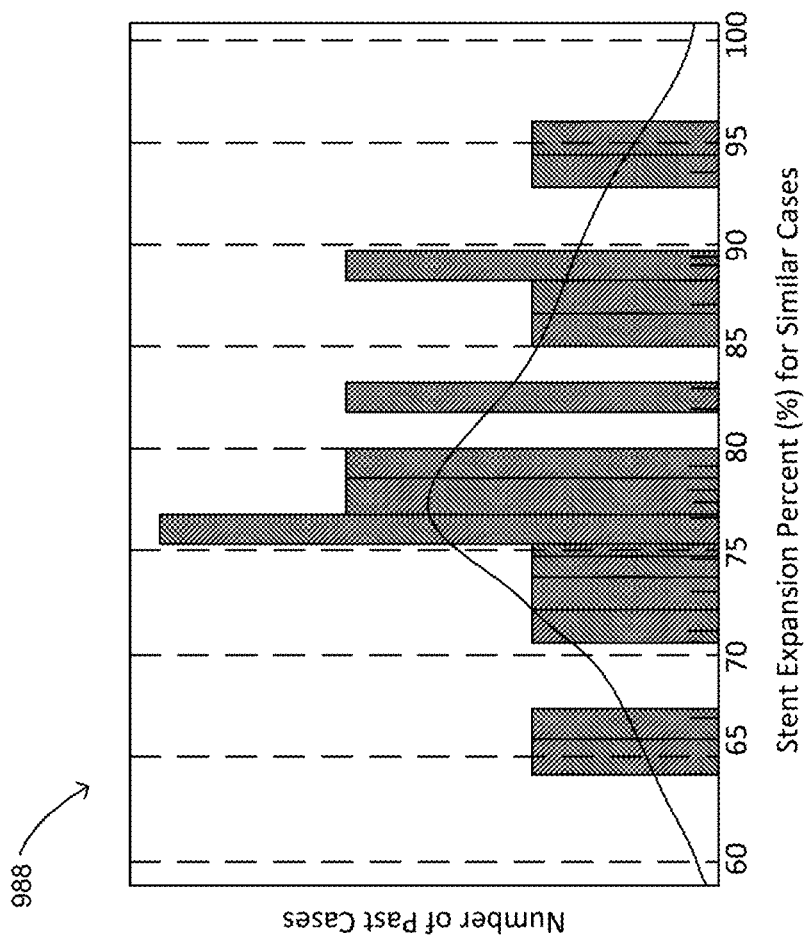
FIG. 9B is an example interface component according to aspects of the disclosure.

According to some examples, the display 918 may additionally or alternatively include a histogram, such as histogram 988 shown in FIG. 9B. The histogram 988 may graphically present information regarding stent expansion for similar cases. As shown, histogram 988 graphically illustrates the percent stent expansion for similar cases and the number of cases. As described above, similar cases may be determined based on a machine learning model.

The data used to create the histogram may be based on a similarity metric. According to some examples, the similarity metric may change based on the machine learning model selected. For example, if a linear model like regression is selected, a Euclidian distance metric weighted by the coefficients of the logistic regression may be used. Additionally or alternatively, if a decision tree ensemble is selected, a histogram may be generated based on cases that fall into the same leaf nodes as the test case. In either case, whether a linear like model or a decision tree ensemble is selected, each histogram may be augmented by displaying risk estimates for different balloon sizes and pressures. This may provide the user with some idea of whether risk can be mitigated by balloon choice.

Figure 10:
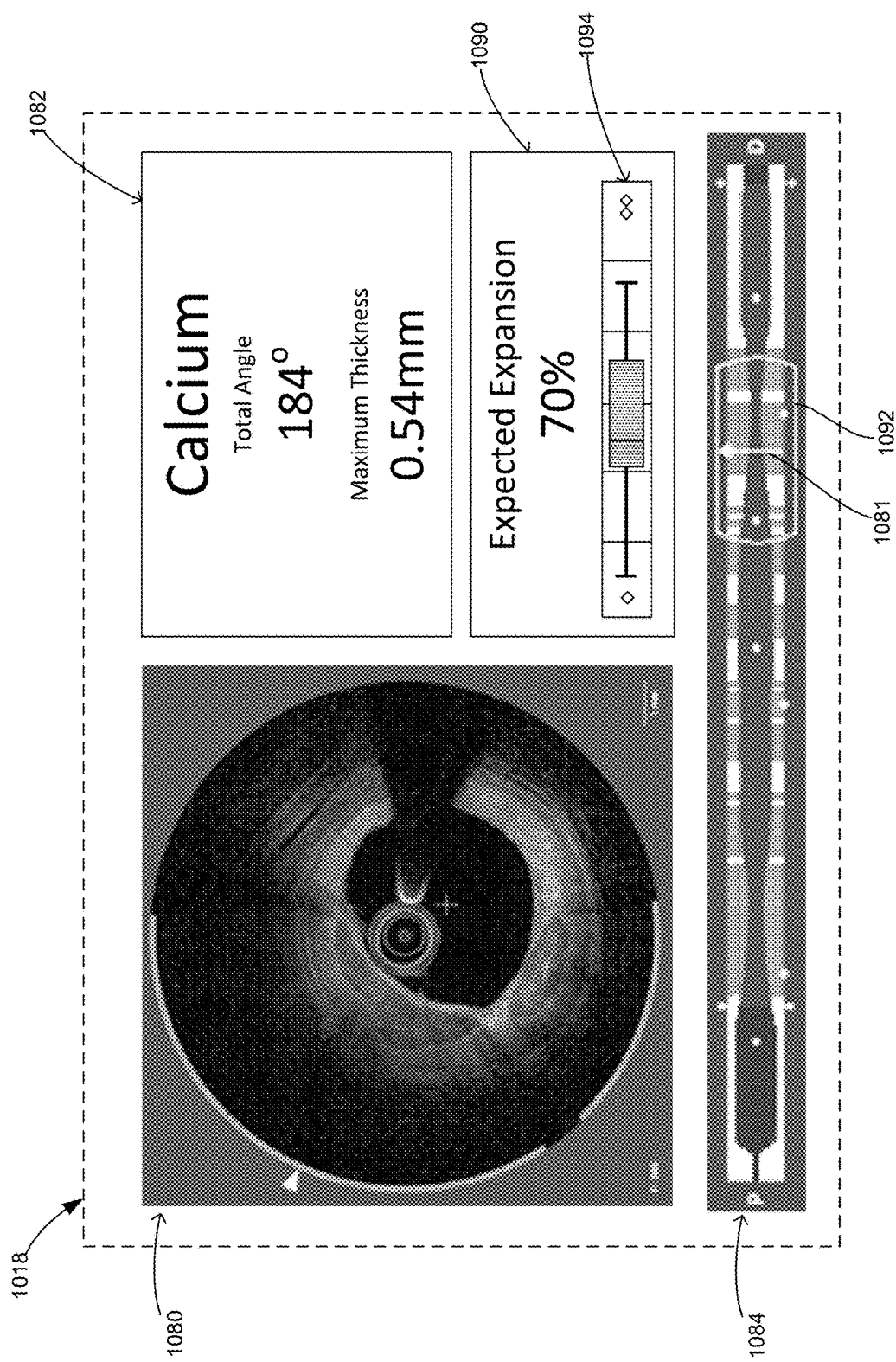
FIG. 10 is an example display according to aspects of the disclosure.

FIG. 10 illustrates an example display including the risk assessment and the predicted stent expansion. Similar to the display shown in FIG. 9, display 1018 may include a longitudinal representation 1084 of the blood vessel, the selected frame 1080 within the longitudinal representation 1084, an information display 1082, and an expected expansion display 1092. The longitudinal representation 1084 may include an indication or marker 1081 identifying the selected frame 1080. While not shown, the display 1018 may additionally or alternatively include one or more of the interface components described above. For example, display 1018 may include the stent expansion risk, as shown in FIG. 9A or a histogram, as shown in FIG. 9B.

The information display 1082 may include information regarding the calcium burden, such as the total angle and the maximum thickness. However, this is merely one example. The information display 1082 may include information pertaining to any arterial feature, such as visible media, the presence of lipidic plaque or thin-capped fibroatheroma, measurements of the lumen diameter and eccentricity, etc. The visible media may include the external elastic lamina.

The expected expansion display 1090 may be the predicted stent expansion based on the detected arterial features. For example, the calcium burden may be determined based on the image data obtained from one or more pullbacks. The expected expansion may be shown as a percentage of the expected expansion, such as the 70% shown. Additionally or alternatively, a box plot 1094 may be included in the expected expansion display 1092. The box plot 1094 may indicate a range of likely expansions.

Figure 11:
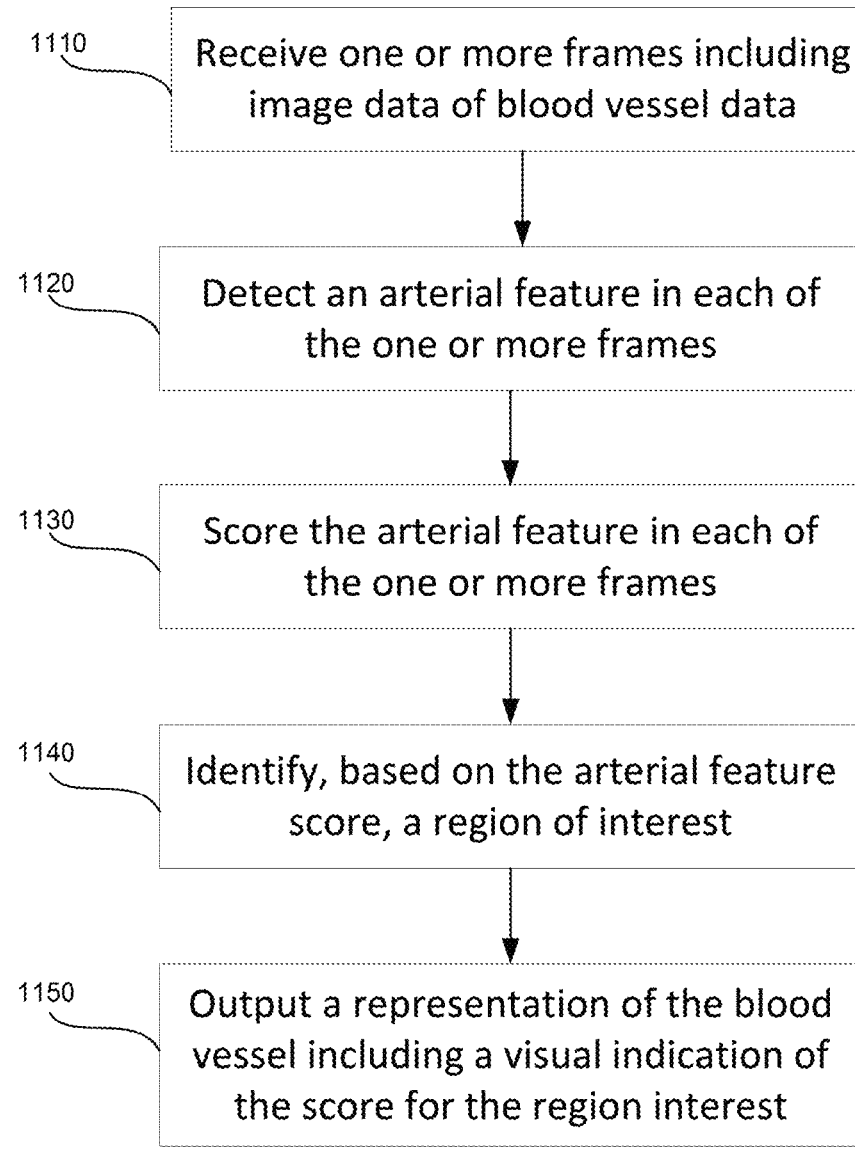
FIG. 11 is a flow diagram illustrating a method of outputting a representation of a blood vessel according to aspects of the disclosure.

FIG. 11 illustrates an example method of outputting a representation of a blood vessel. The following operations do not have to be performed in the precise order described below. Rather, various operations can be handled in a different order or simultaneously, and operations may be added or omitted.

For example, in block 1110 one or more processors may receive one or more frames including image data of a blood vessel segment. The frames may be obtained during one or more imaging pullbacks. For example, the pullbacks may be taken pre-treatment, post-treatment, pre-stenting, post-stenting, pre-artherectormy, post-artherectomy, pre-angioplasty, post-angioplasty, post-optimization, etc. According to some examples, the pullbacks may be taken after stenting and/or after the physician has further ballooned the stent with various balloon diameters and pressures.

In block 1120, the one or more processors may detect an arterial feature in each of the one or more frames. The arterial feature may be, according to some examples, the calcium burden, visible media, the presence of lipidic plaque or thin-capped fibroatheroma, measurements of the lumen diameter and eccentricity, etc In block 1130, the one or more processors may score the arterial feature in each of the one or more frames. The score may be a stent under-expansion risk score. The score may be determined using a machine learning model. The machine learning model may compare pre-PCI information and post-PCI outcomes for each case.

In block 1140, the one or more processors may identify, based on the arterial feature score, a region of interest. In examples where the score is a stent under-expansion risk score, the region of interest may be a region of calcium burden. Additionally or alternatively, in examples where the score is a stent under-expansion risk score, the region of interest may be a region in which there is a high, moderate, or low risk of stent under-expansion.

In block 1150, the one or more processors may output a representation of the blood vessel segment including a visual indication of the score for the region of interest. The representation may be a two-dimensional and/or three-dimensional representation. The visual indication of the score may be a color-coded indication. The indication may be color-coded based on the arterial feature score. For example, if the score is the stent under-expansion risk score, the color of the indication may be red, yellow, or green. A red indication may indicate that there is a high risk of stent under-expansion, yellow may indicate that there is a moderate risk, and green may indicate that there is a low risk of stent under-expansion. In some examples, such as when the display is not a color display, the indication may be color coded in greyscale.

The indication may be in the shape of a bar, such as a rectangle, that is parallel to the longitudinal axis of the representation of the blood vessel. The bar may extend the length of the arterial feature in the representation. In examples where the arterial feature is calcium burden, the bar may extend the length of the calcium burden in the representation. Based on the color of the bar, the physician may quickly recognize that the calcium burden may or may not pose a risk to stent under-expansion.

User Workflow

The computing device, described above, may assist an end user in navigating through lesion assessment, stent sizing, deployment, and post-deployment assessment. For example, the computing device may output lesion morphology. The output may be in a way that allows the end user the ability to easily assess the lesion morphology. According to some examples, the output may include a color coded representation of the blood vessel segment. Each color in the color coded representation may represent a level of severity. Additionally or alternatively, each color in the color coded representation may represent a predicted, estimated, or determined stent under-expansion risk based on an arterial feature. The arterial feature may be, for example, the calcium burden. A color coded risk estimate may motivate, encourage, and/or allow the user to adapt their vessel preparation and/or stenting strategy. For example, if the risk posed by calcium is high, the user may see at least a portion of the vessel as red, representing a high risk. According to some examples, instead of or in addition to color coding, the level of risk may be shown in greyscale, as hatching, etc. Thus, color coding is merely one example and is not intended to be limiting.

By quickly and easily assessing the high risk of stent under-expansion represented by a specific color, the user may determine to change the treatment plan. For example, if the risk posed by the calcium burden is high and the user sees a lot of red, the user may choose to do more aggressive ballooning or vessel preparation prior to stent deployment. In some examples, a high risk may indicate to the user that they should adapt an atherectomy technique to remove or fracture the calcium prior to stent deployment, using technologies such as cutting balloons, scoring balloons, orbital or rotational drills, ultrasound lithotripsy, etc.

According to some examples, the color coded representation may allow the user to forgo stenting on a particular lesion and, instead, focus on a different lesion, such as a lesion with a higher risk. In some examples, the user may, based on the color coded representation, perform a more aggressive post-dilation after stent deployment.

The computing device, based on the color coded representation, may provide a suggested a balloon size and/or type. For example, based on the machine learning models, described above, the computing device may predict and, therefore, suggest, the balloon size and/or type based on similar cases. Additionally or alternatively, the computing device may provide a suggested use of the device. The suggested use may be based on the particular plaque morphology of the segment of the blood vessel. In some examples, the suggested use of the device may be based on a machine learning model focused on device usage in a per case basis.

The invention claimed is:

1. A method, comprising:
   receiving, by one or more processors, one or more frames including image data of a blood vessel segment;
   detecting, by the one or more processors, an arterial feature in each of the one or more frames, wherein the arterial feature is an under-expansion risk;
   scoring, by the one or more processors, the arterial feature in each of the one or more frames;
   determining, by the one or more processors using a machine learning model, the under-expansion risk, wherein the machine learning model compares pre-percutaneous intervention ("PCI") data and post-PCI data for a plurality of cases;
   identifying, by the one or more processors based on the arterial feature score, a region of interest; and
   outputting, by the one or more processors based on the arterial feature score, a representation of the blood vessel segment including a visual indication of the score for the region of interest.

2. The method of claim 1, wherein the detected arterial feature is a calcium burden.

3. The method of claim 1, wherein the under-expansion is a stent under-expansion risk.

4. The method of claim 3, wherein the visual indication of the stent under-expansion risk is a color-coded indication.

5. The method of claim 4, wherein the color-coded indication is based on a severity of the under-expansion risk.

6. The method of claim 1, wherein scoring the arterial feature in each of the one or more frames is based on a sliding window measure.

7. The method of claim 1, wherein the visual indication of the score is a bar parallel to a longitudinal axis of the representation of the blood vessel and extends along the region of interest.

8. The method of claim 7, wherein the bar is color-coded based on the arterial feature score.

9. The method of claim 8, wherein the arterial feature score is a stent under-expansion risk.

10. A device, comprising:
one or more processors configured to:
receive one or more frames including image data of a blood vessel segment; detect an arterial feature in each of the one or more frames, wherein the arterial feature is an under-expansion risk;
score the arterial feature in each of the one or more frames;
determine, using a machine learning model, the under-expansion risk, wherein the machine learning model compares pre-percutaneous intervention ("PCI") data and post-PCI data for a plurality of cases;
identify, based on the arterial feature score, a region of interest; and
output, based on the arterial feature score, a representation of the blood vessel segment including a visual indication of the score for the region of interest.

11. The device of claim 10, wherein the detected arterial feature is a calcium burden or an under-expansion risk.

12. The device of claim 11, wherein the under-expansion is a stent under-expansion risk.

13. The device of claim 10, wherein scoring the arterial feature in each of the one or more frames is based on a sliding window measure.

14. The device of claim 10, wherein the visual indication of the score is a bar parallel to a longitudinal axis of the representation of the blood vessel and extends along the region of interest.

15. A non-transitory computer-readable medium storing instructions executable by one or more processors for performing a method, comprising:
receiving one or more frames including image data of a blood vessel segment;
detecting an arterial feature in each of the one or more frames, wherein the arterial feature is an under-expansion risk;
scoring the arterial feature in each of the one or more frames;
determining, using a machine learning model, the under-expansion risk, wherein the machine learning model compares pre-percutaneous intervention ("PCI") data and post-PCI data for a plurality of cases:
identifying, based on the arterial feature score, a region of interest; and
outputting, based on the arterial feature score, a representation of the blood vessel segment including a visual indication of the score for the region of interest.

* * * * *